(12) United States Patent
Park et al.

(10) Patent No.: US 11,076,916 B2
(45) Date of Patent: Aug. 3, 2021

(54) THERMAL ACCELERANT COMPOSITIONS AND METHODS OF USE

(71) Applicants: Rhode Island Hospital, Providence, RI (US); Brown University, Providence, RI (US)

(72) Inventors: William Keun Chan Park, Westerly, RI (US); Damian E. Dupuy, Centerville, MA (US)

(73) Assignees: Rhode Island Hospital, Providence, RI (US); Brown University, Providence, RI (US)

( * ) Notice: Subject to any disclaimer, the term of this patent is extended or adjusted under 35 U.S.C. 154(b) by 33 days.

(21) Appl. No.: 16/708,416

(22) Filed: Dec. 9, 2019

(65) Prior Publication Data
US 2020/0179049 A1    Jun. 11, 2020

Related U.S. Application Data

(63) Continuation-in-part of application No. 15/389,809, filed on Dec. 23, 2016, now Pat. No. 10,722,289.
(Continued)

(51) Int. Cl.
*A61K 45/06* (2006.01)
*A61B 18/18* (2006.01)
(Continued)

(52) U.S. Cl.
CPC .......... *A61B 18/1815* (2013.01); *A61B 18/14* (2013.01); *A61K 45/06* (2013.01);
(Continued)

(58) Field of Classification Search
CPC ................ A61B 18/14; A61B 18/1815; A61B 2018/00095; A61B 2018/00577; A61B 2018/00982; A61K 45/06
See application file for complete search history.

(56) References Cited

U.S. PATENT DOCUMENTS

2004/0210282 A1   10/2004   Flock et al.
2008/0171982 A1   7/2008   Mehier
(Continued)

OTHER PUBLICATIONS

International Search Report and Written Opinion for International Patent Application No. PCT/US2020/064082 dated Apr. 12, 2021, 12 pages.

*Primary Examiner* — Michael F Peffley
*Assistant Examiner* — Bo Ouyang
(74) *Attorney, Agent, or Firm* — Nutter McClennen & Fish LLP

(57) ABSTRACT

A thermal accelerant is delivered to a tissue site and localized to modulate the shape, extent or other characteristic of RF or microwave-induced hyperthermia tissue ablation. The accelerant may be provided via an image-guided hand piece or via a lumen added to a microwave antenna, and promotes faster heating, more complete ablation and/or a more extensive treatment region to reduce recurrence of treated cancers, overcoming natural limitations, variations in tissue response and drop-off or thermal loss away from the antenna. The accelerant is delivered as a viscous but heat sensitive fluid, and is fixed in place to provide regions of preferential absorption or heating. Shorter exposure times to heat the far field may allow survival of vulnerable tissue such as vessels, and multiple antennae may be used for effective treatment of irregular or large tumors.

5 Claims, 13 Drawing Sheets

Related U.S. Application Data

(60) Provisional application No. 62/381,251, filed on Aug. 30, 2016, provisional application No. 62/387,250, filed on Dec. 23, 2015.

(51) Int. Cl.
*A61B 18/14* (2006.01)
*A61B 18/00* (2006.01)

(52) U.S. Cl.
CPC ............... *A61B 2018/00095* (2013.01); *A61B 2018/00577* (2013.01); *A61B 2018/00595* (2013.01); *A61B 2018/00982* (2013.01)

(56) References Cited

U.S. PATENT DOCUMENTS

| | | |
|---|---|---|
| 2011/0152852 A1 | 6/2011 | Cressman |
| 2012/0253188 A1* | 10/2012 | Holland ................. A61B 18/02 600/431 |
| 2013/0053932 A1 | 2/2013 | Wagner et al. |
| 2014/0094793 A1 | 4/2014 | Sharonov |
| 2015/0265725 A1* | 9/2015 | Peyman ................... A61B 5/01 600/2 |
| 2017/0182165 A1 | 6/2017 | Park et al. |

\* cited by examiner

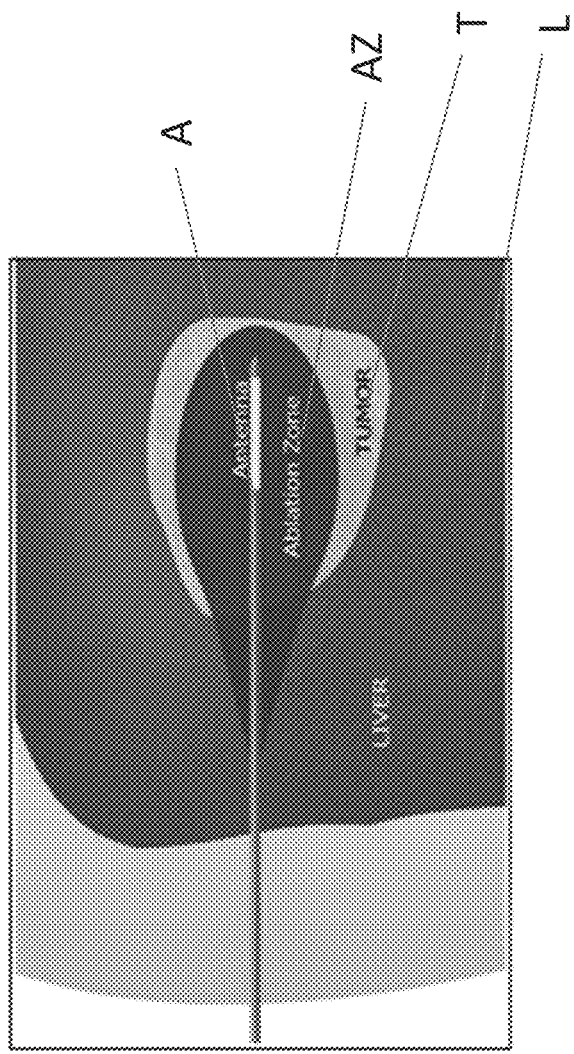
Figure 1A
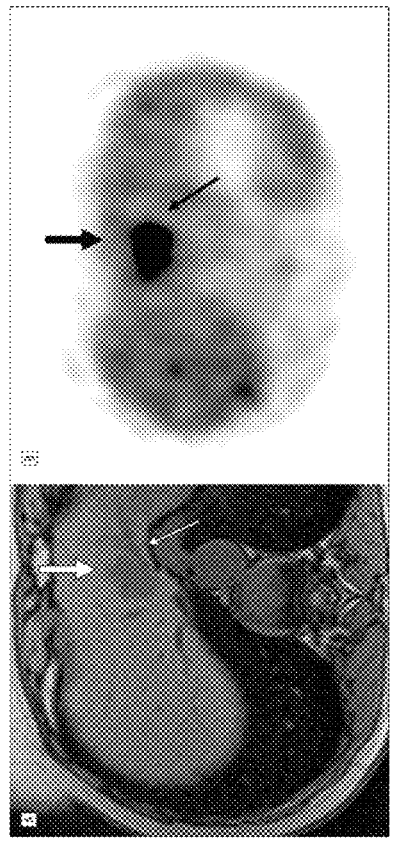
Figure 1B
Figure 1C

THERMAL ACCELERANT COMPOSITIONS AND METHODS OF USE

REFERENCE TO RELATED APPLICATIONS

This application is a continuation-in-part of U.S. application Ser. No. 15/389,809, filed on Dec. 23, 2016, which claims the benefit of Provisional Application Ser. No. 62/387,250 filed Dec. 23, 2015 and Ser. No. 62/381,251 filed Aug. 30, 2016 in the United States Patent & Trademark Office. The three above noted patent applications are hereby incorporated herein by reference, in their entireties, including their drawings and appendices.

TECHNICAL FIELD

The present invention relates to methods, materials and equipment for hyperthermal tissue ablation, that is, to the application of energy to heat and destroy tissue such as a tumor located in an internal organ, vessel, bone or other site, without surgery. Among the instruments used for such ablation are monopolar (MP) radiofrequency antennae; bipolar (BP) radiofrequency electrodes; and microwave antennae. These may be inserted transdermally, or via a catheter sheath to access a treatment site, and each has its characteristic action and actuation parameters. The use of such an antenna device for locally heating tissue to achieve hyperthermal tissue ablation may require a characteristic operating duration, applied power level and frequency and type of electromagnetic drive, and the proper selection or setting of these parameters and positioning of the antenna tip will generally depend upon the tissue type as well as the size and shape of the target tumor. Among the different heating modalities, microwave ablation may be applied to internal tissue sites using a needle-like antenna carried in a probe or hand piece, and the active antenna may be imaged, for example by CT imaging, to guide placement precisely in relation to a target tissue site. The target itself may be, or have been, identified by diagnostic imaging, by the same or another medical imaging modality.

Such image-guided microwave tumor ablation has been recognized as a safe, minimally invasive and cost-effective cancer treatment for discrete tumors, and may sometimes be a treatment of choice when other factors render surgery dangerous or otherwise inadvisable.

However, while placement of the microwave antenna may be made anywhere in the body using a simple surgical ablation needle hand piece or commonly available trocar and catheter for placement of the antenna and cable, as appropriate for the intended target site, the effective heating range of a microwave ablation antenna results in an oval- or oblong-shaped ablation region that extends only a relatively small distance around the ablation antenna. Its heating effects may vary, to some extent, depending on the local tissue conditions. While this short effective range will limit unintended damage to most nearby healthy tissue structures, it also presents a drawback, in that microwave ablation drops off rapidly in only a few centimeters, and the ablation may be irregular due to either the rate of microwave heat generation at the site, or heat conduction away from the site into adjacent tissue, or variations in tissue conductivity and dielectric constant (which may be different for each patient). As a result, when treated by microwave hyperthermal ablation, tumors experience a relatively high rate of recurrence (ca. 30%) due to loci of incomplete ablation. The incomplete ablation and consequent tumor cell survival and tumor recurrence may occur because some undetected tumor cells lie outside of the effective ablation zone; because local variations of the tissue characteristics result in intrinsically lower heat generation; because surviving tumor cells are in the vicinity of a blood vessel that acted as a 'heat sink' limiting the temperature rise in a portion of the targeted region during the ablation procedure by increasing thermal conduction away from the intended ablation site; or because the drop-off or shadowing in the far field resulted in great variations of effective temperature around the nominal target temperature.

The effective ablation zone for a microwave needle/antenna is typically an almond-shaped region extending only 2-4 cm from the microwave antenna, as shown in FIG. 1A, which illustrates a microwave needle/antenna A inserted into a tumor T in a patient's liver L such that actuation heats an ablation zone AZ that covers the center, but not the fringes, of the tumor. FIG. 1B shows an actual image of a real-life liver tumor that had metastasized from and presented with a left-side colon cancer. Following resection of the colon primary, the patient was treated with 8 cycles of leucovorin, fluorouracil, and oxaliplatin, as well as bevacizumab (Avastin). The liver tumor, however, was deemed unresectable owing to concerns about functional liver reserve, so it was treated by microwave ablation of tumors in several segments, of which one is indicated by the thick arrow in FIG. 1B. The tumor measured 2.7 cm and abutted the left hepatic vein (thin arrow). Following the ablation procedure a follow-up Positron-emission tomographic scan image was taken. As shown in FIG. 1C, increased fluorodeoxyglucose activity (thick arrow) was observed in a small region, at a location consistent with the presence of residual tumor adjacent to the left hepatic vein (FIG. 1C, thin arrow). Heat sink was implicated as a possible contributing cause of the residual disease. The patient was alive 3 years after initial diagnosis.

Other factors may contribute to sub-optimal ablation efficacy, including incomplete knowledge of the target tissue and its microwave heating characteristics, irregular shape or size of the target, and presence of tissue that limits access or placement of the antenna.

It would therefore be highly desired to provide improved compositions, devices and methods for microwave hyperthermal ablation treatment to address the aforesaid problems of incomplete or irregular ablation, and thereby operate to reduce incidents of tumor recurrence.

It would also be desirable to provide a means to shape, control, enhance or more quickly effect hyperthermal microwave ablation of an intended transdermal target site.

It would also be desirable to provide compositions that mitigate or overcome tissue-dependent temperature variations to enable uniform and effective ablation of diverse tissues and organs.

SUMMARY OF THE INVENTION

In accordance with some embodiments of the present invention, methods and systems ablate tissue. To that end, the methods and systems may introduce a first applicator to a target site in a patient; position a first thermal accelerant to define a nominal ablation zone for the target site, the thermal accelerant comprising a chaotrope; and activate the first applicator to excite particles of the first thermal accelerant for heating the first thermal accelerant to a specific temperature to ablate the target site.

In some embodiments, the method can further apply the first thermal accelerant to a surface of a tissue at a target site to cauterize the target site. In some embodiments, positioning the first thermal accelerant can further include positioning the accelerant at an outer-boundary of the target site. Moreover, the method can further introduce a second applicator or a second thermal accelerant to the target site, the second applicator and the second thermal accelerant being positioned in a substantially rhombal shape with the first applicator and the first thermal accelerant. Further, the first applicator or the second applicator can include an electrode having one or more energy emitting devices thereon. Further still, the method can further include passing one or more of the first applicator and the first thermal accelerant through the target site under image guidance. Among other things, the first thermal accelerant may coagulate to become integral with the ablated tissue. In some embodiments, the specific temperature can be between approximately 60 degrees Celsius to approximately 170 degrees Celsius.

In accordance with alternate embodiments of the present invention, the first thermal accelerant may include material having a high dipole moment that is configured to convert radiofrequency to thermal energy. The first thermal accelerant may be positioned to enhance heating by applying electric energy in a far field, peripheral drop-off, or tissue variation region to thereby extend ablation effects to said regions. The dipole moment may have a value that ranges from about 7 Debye to about 1,000 Debye. Among other things, the first applicator can emit one or more of microwave energy, radiofrequency energy, and a pulse of energy of electroporation. The target site can include one or more of a tumor and a tissue target in a patient.

In accordance with alternate embodiments of the present invention, the first thermal accelerant may remain substantially stationary within the target site after deposition. Among other things, the first thermal accelerant may be positioned between the first applicator and healthy tissue to prevent healthy tissue from overheating. In some embodiments, the method can further include positioning the first thermal accelerant between an ablation site and a heat sink to modulate conduction of heat away from the ablation site. Moreover, the method can include delivering the thermal accelerant from the first applicator.

In accordance with other embodiments, various compositions of thermal accelerant can be used for ablation. The composition can include a thermal accelerant having a polymer configured to become gelatinous or solidify at body temperature or above to become relatively immobilized after positioned within the target site, a chaotrope configured to adjust charge distribution within the polymer, and an imaging component configured to allow image-guided verification of the thermal accelerant within a body of a patient. The thermal accelerant, when exposed to an amount of ablative energy, has values of electrical conductivity and loss factor that are up to 5 times or greater than values of electrical conductivity and loss factor in living tissue when exposed to an equal amount of ablative energy without thermal accelerant The viscosity of the thermal accelerant can range from approximately 50 centiPoise to approximately 25,000 centiPoise. The chaotrope can be selected from the group consisting of: calcium chloride, cesium chloride, lithium chloride, potassium chloride, rubidium chloride, sodium chloride, sodium citrate, and a combination thereof. In some embodiments, the cesium chloride may tumble synchronously to the alternating electric field fueled by its intrinsic dipole moment to generate heat. Moreover, the polymer can include one or more of albumin, DNA, RNA, glycoproteins or glycopolymers such as IgA, IgG, or other immunoglobulins.

BRIEF DESCRIPTION OF THE FIGURES

These and other features of the invention will be understood from the Figures and Description below, taken together with the Claims appended hereto, wherein FIG. 1A schematically shows non-overlapping ablation and tumor regions of a prior art microwave hepatic tumor ablation treatment;

FIG. 1B shows a metastatic tumor in the liver of a patient and abutting the hepatic vein;

FIG. 1C is a PET scan of that site showing residual tumor growth suggesting that heat sink effect was a contributing cause of the residual disease;

DETAILED DESCRIPTION

Figure 2A:
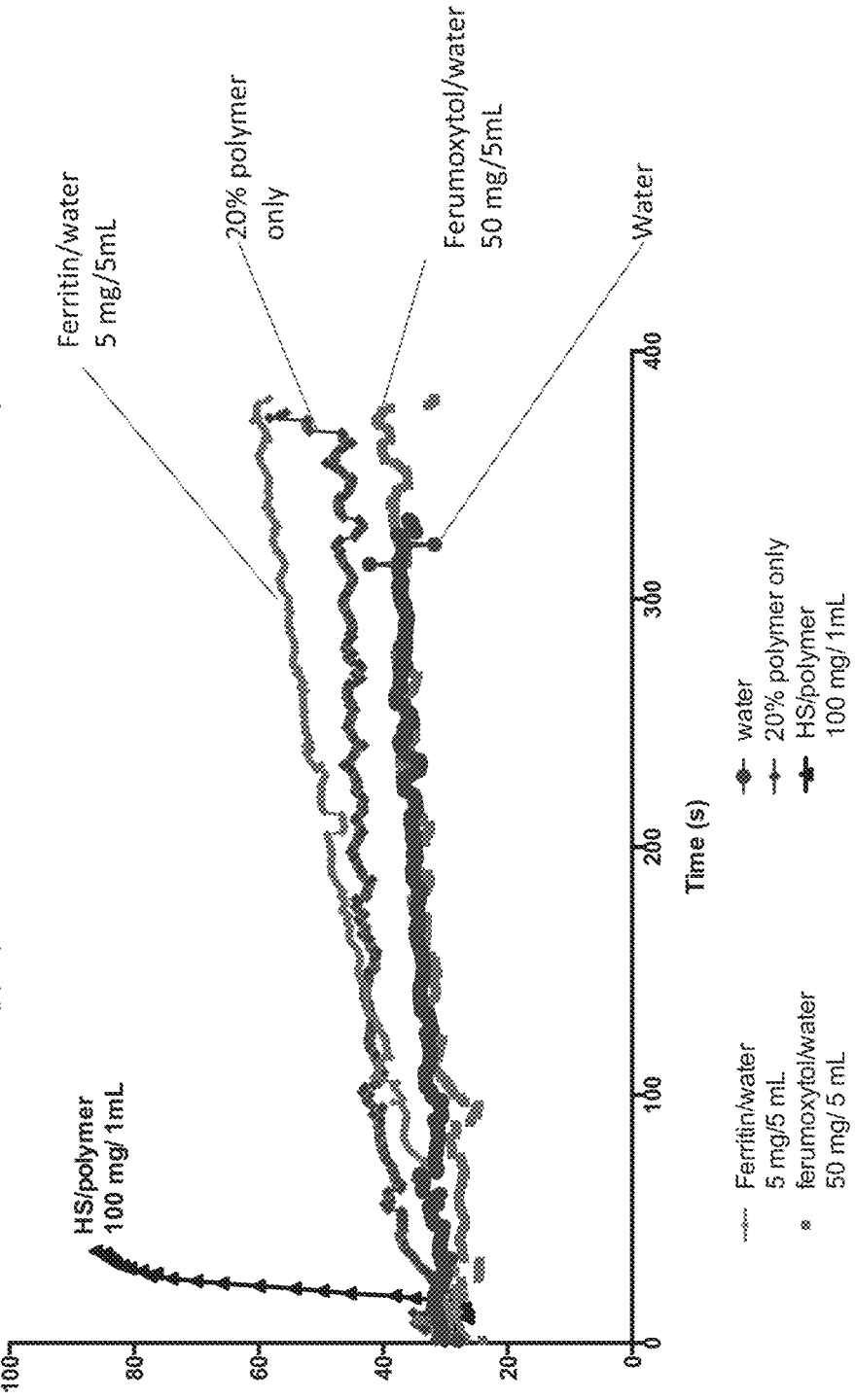
FIG. 2A shows effective rates of temperature increase by microwave heating for different fluids.

In its broadest form the invention includes application of a strong energy absorber, a 'heat substrate' (HS) or 'thermal accelerant' (TA) to a tissue site to locally modulate the rate, extent or endpoint of temperature increase to achieve effective hyperthermal ablation of the tissue with a microwave or radio frequency (RF) antenna, such as an image-guided transdermal microwave antenna, and overcome the limitations or problems raise by the limited range, high variance in temperature distribution and tissue-caused artifacts such as shadowing and heat sink. In one initial embodiment, a reverse phase polymer is used as a carrier and is injected to a fluid to desired locations in or around a relevant tissue site. The polymer is liquid, and it gels, becomes gelatinous or even solidifies at body temperature or above, so it either is, or quickly becomes, immobilized and stays localized at the delivery site. The polymer may be one that changes state and expels liquid (e.g., water) at temperatures consistent with ablation procedures. In one embodiment, the polymer also contains a salt; use of cesium chloride has been found to greatly increase the microwave/heating interaction and also to render the accelerant visible under CT or MIII, thus allowing image-guided verification of localization prior to RF or microwave excitation. Other imaging modalities, such as ultrasound may be used for image guidance. The polymer with appropriate characteristics may be one such as a block-co-polymer PLGA-PEG-PLGA consisting of polyethylene glycol, which is covalently esterified by an FDA-approved poly lactic-co-glycolic acid on both ends. In operation, a range of parameters may be varied to establish ablation response as a function of microwave conditions (i.e., power, frequency, ablation period and distance) in a representative tissue, such as a pig or calf liver. (see, for example, the modeling protocols in Pillai K, Akhter J, Chua T C, Shehata M, Alzahrani N, Al-Alem I, Morris D L. 2015. Heat sink effect on tumor ablation characteristics as observed in monopolar radiofrequency, bipolar radiofrequency, and microwave, using ex vivo calf liver model. Medicine (Baltimore) 94(9):e580). In another embodiment the thermal accelerant is a preparation of a serum albumin or other albumin, as described further below, together with certain electrolytes that condition its viscosity, microwave energy absorbance or thermal accelerant properties, and preferably also provide imaging under one or more medical imaging modalities such as MM, ultrasound or x-ray CT imaging.

Example 1

To mitigate the problem of inadequate heating, applicants devised a novel heat substrate to selectively increase heating and, by suitable placement, avoid undesirable cooling or 'heat sink' effects. This substrate is made of cesium chloride (CsCl) and is compounded in a reverse phase transition polymer to be positioned, and then activated by microwave energy from a distance. The reverse phase transition polymer, which may, for example be a PLGA-PEG-PLGA block copolymer of suitable viscosity, transforms into a gel at body temperature or above and with the cesium chloride salt strongly responds to microwave radiation and locally increases the temperature to more effectively ablate tumor cells that lie just outside of ablation zone AZ of FIGS. 1A, 1B and 1C. Furthermore, this heat substrate is an excellent contrast agent by itself, and was found to be visible under CT imaging. These properties make it particularly efficacious for treating solid tumors, where a physician can control the amount, the location(s) and the concentration of the heat substrate delivered to and fixed at locations about the targeted tumor to ensure complete ablation. Moreover, for larger or irregularly-shaped tumors, several microwave antennae may be positioned under image guidance to completely cover the tumor with a corrected/enhanced heat distribution.

Figure 2B:
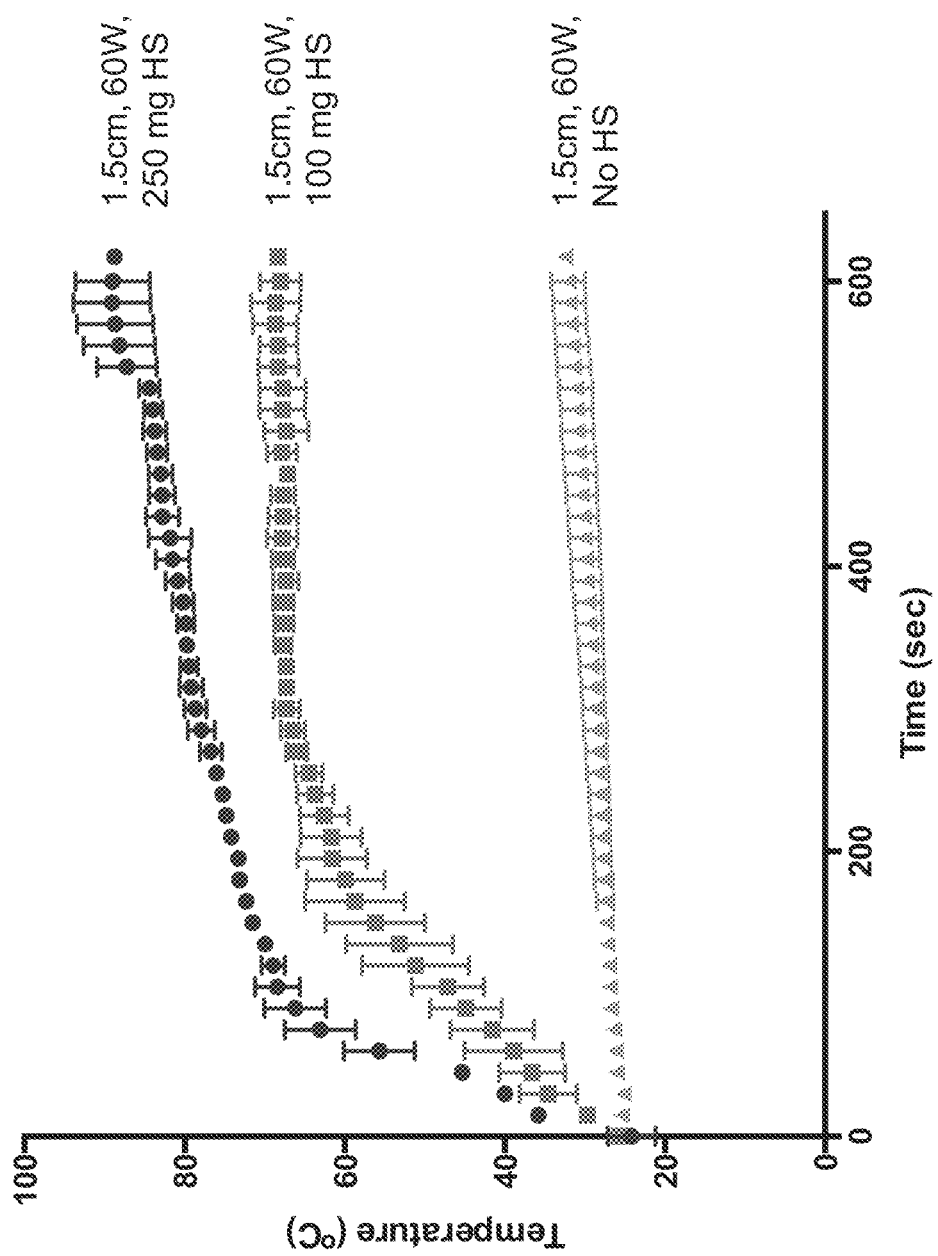
FIG. 2B shows effective rates of temperature rise for untreated tissue and for different heat substrate formulations.
Figure 2C:
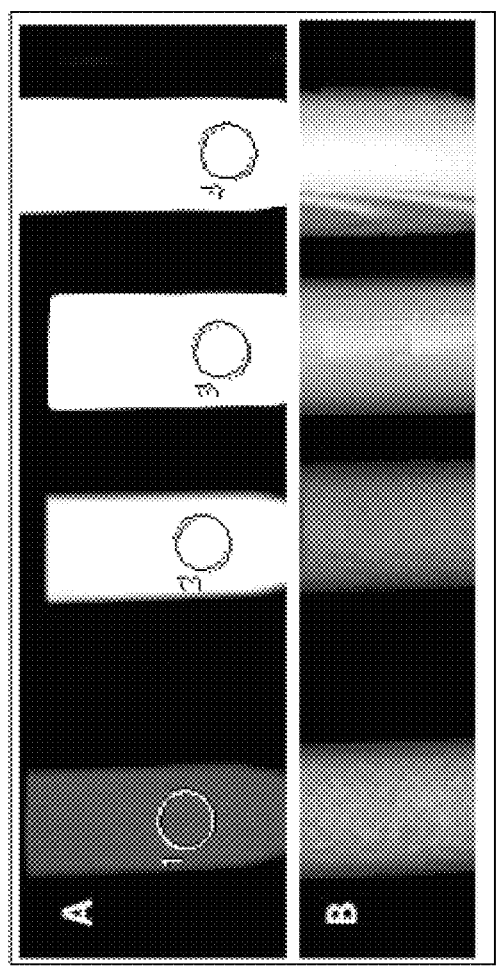
FIG. 2C shows small vials of distilled water and three different concentrations of a HS, confirming discernable contrast and detectability under CT imaging.

Various investigations were performed to assess the degree of heating achievable by the CsCl heat substrate compounded with different salt concentrations. FIG. 2A specifically shows that the heat substrate picks up microwave energy in a distance to augment heating, with high CsCl concentration of 100 mg/ml greatly increases heating measured near to (1 mm) the antenna, and that enhance heating with high uniformity is attained with other concentrations measured 15 mm away from the antenna (FIG. 2B). The Figures specifically illustrate the effect of heat substrate (100 mg/mL, CsCl/20% (w/v) polymer) on temperature increase by microwave energy (15 W, 915 MHz, t=400 sec) in FIG. 2A, where the temperature increase was monitored 1 mm away from the antenna; and the effect of heat substrate (0, 100, 250 mg/mL, CsCl/20% (w/v) polymer) on temperature increase by microwave energy (60 W, 915 MHz, t=600 sec) where heat substrate is deposited 15 mm from the MW antenna. There is a significant augmentation of heat when the heat substrate is present. Moreover the salt/polymer heat substrate is an excellent contrast agent visible through CT as shown in FIG. 2C. In that Figure fixed volumes of different concentrations of the salt preparation and of distilled water were imaged under CT and their Hounsfield absorbance noted to be: 1. Distilled water −15 Hu, 2. HS (10 mg/mL) 286 Hu, 3. HS (100 mg/mL) 2056 Hu, 4. HS (1000 mg/mL) 3070 Hu. The lower portion of FIG. 2C shows the same samples with computer-aided enhancement. Even the lowest concentration 10 mg/mL HS yields a discernable contrast comparing to water in CT. The imaging was performed using a GE Optima 580 W CT scanner with CT protocol: 120 kV, 50 mA, 0.8 second rotation, 0.562:1 pitch, and 16×0.625 mm detector configuration. The radiation output (CTDIvol) was 12.08 mGy, and the Dose Length Product was 193.88 mGy-cm.

Figure 2D:
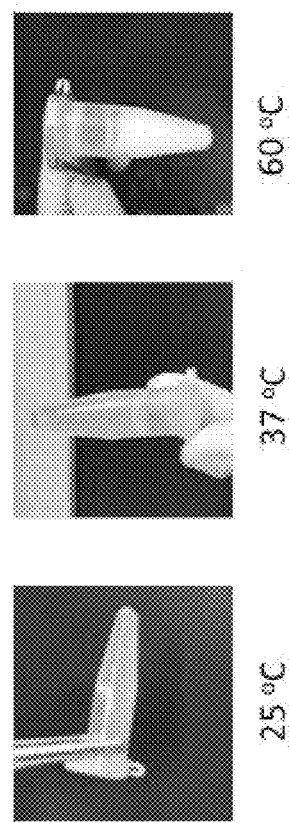
FIG. 2D shows a polymer/salt agent undergo liquid-gel-precipitate changes with temperature rise.

FIG. 2D illustrates the phase change properties with increasing temperature when the CsCl salt is compounded with polymer.

Temperature-time plots were made for different concentrations, together with pictures of the substrate changes when deposited and microwaved in an ex-vivo liver and these confirmed that the heat substrate is capable of heating liver tissue 15 mm away from the antenna, and that the substrate can be deposited as a liquid at ambient temperature and turns into a gel once in body, allowing the tumor boundary to be precisely targeted to ensure complete ablation. In that study a whole calf liver was heated with MW energy (60 W, 915 MHz): and a small 350 μL volume of 100 mg HS in 20% (w/v) polymer solution was injected to a point 1.5 cm away from the tip of the MW antenna. After 10 minutes, the area was cut open to observe the polymer solution transformed into a precipitate. The temperature increase was seen to be proportional to the HS concentration. At 250 mg/mL, the temperature reached 60° C. within 3 minutes. At 100 mg/mL, it took approximately 5 minutes whereas the temperature increase was nominal when no HS had been applied.

The investigations of Example 1 thus demonstrated the value of the heat substrate. Further investigations were designed and/or carried out to model or assess heating characteristics of the compositions in specific tumor tissues or specific distances, as well as evaluating imageability of representative formulations (see the discussion of FIG. 2C, supra) to better support use of the heat substrate in clinical procedures and new methods of treatment. Specifically, the heat substrate may be suitably positioned in relation to the microwave antenna, so that application of microwave energy produces a tailored heating profile to heat up and ablate the surrounding tissue. For example, the accelerant may be positioned somewhat away from the antenna to enhance heating of peripheral tissue which is too distant to be fully or uniformly ablated using a single microwave antenna alone. The thermal accelerant can also be positioned to prevent the heat loss (also known as "heat sink" see FIG. 1C—that would otherwise occur due to the presence of a large blood vessel in or adjacent to the intended ablation zone, trapping an effective level of heating in the near field without ablating the blood vessel itself. Modeling was performed for the use of multiple antennae, and for more than one localized body of thermal accelerant strategically placed to define a larger, or more uniform and expanded ablation zone, or to define an ablation zone while limiting the time that power is applied to other portions of the organ. Thus the thermal accelerant plays a cooperative and synergistic role in augmenting the effective microwave energy. The suitability for each of these interventions, however, will require that the actual level of increased heating be sufficient to overcome any countervailing conduction and absorption effects exerted by surrounding tissue.

A pilot study was designed to establish the actual thermal accelerant response as a function of microwave conditions (i.e., power, frequency, ablation period and distance) in pig's liver. Ideally, the thermal accelerant augments the microwave energy transmitted through the antenna, and it was expected that the thermal accelerant turns into a gel, once injected, in the target area of the body. Upon application of the microwave energy, the thermal accelerant will heat up the surrounding tissue, which is too distant to be ablated with single microwave antenna alone.

Figure 3A:
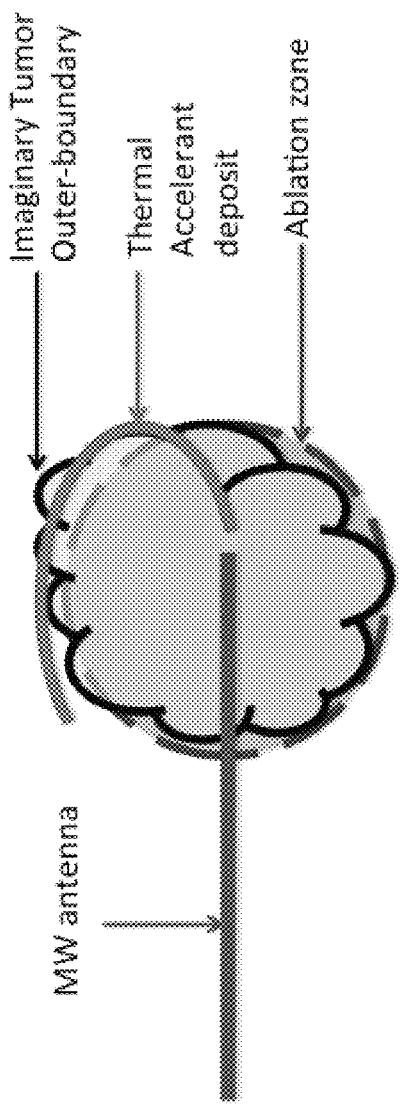
FIG. 3A schematically shows a tumor and placement of antenna and thermal accelerant.
Figure 3B:
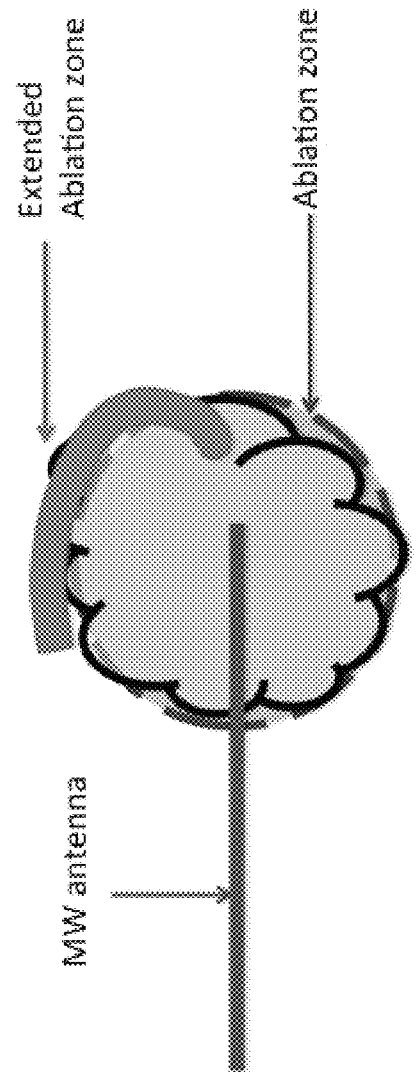
FIG. 3B shows extension of ablation with the placement of FIG. 3A.
Figure 4:
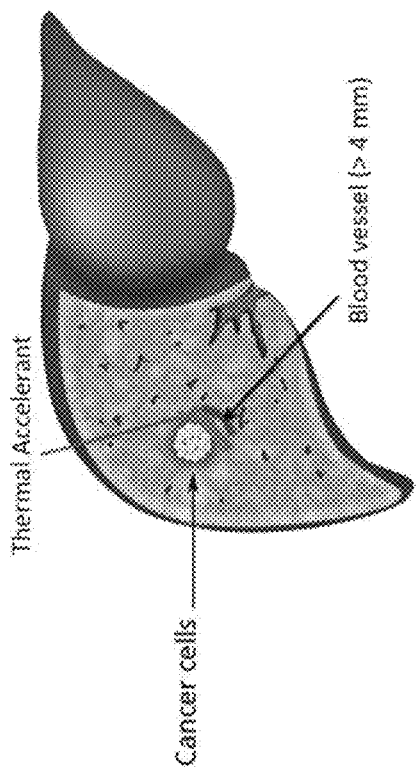
FIG. 4 shows a liver section and placement of thermal accelerant between a tumor and a blood vessel.
Figure 5:
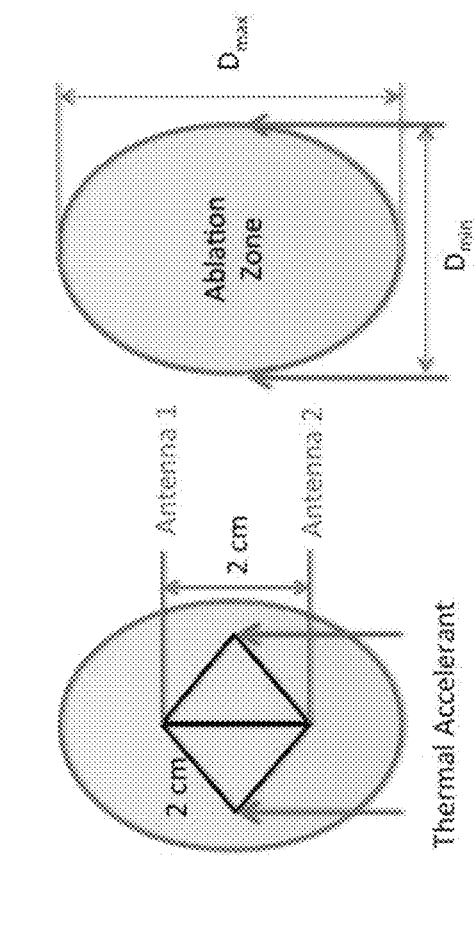
FIG. 5 shows placement of two antennas and two sites of thermal accelerant for creating an enlarged ablation zone.

This situation is illustrated schematically in FIG. 3A and FIG. 3B wherein a small mass of the substrate located at the upper right distal region or surface of an irregular tumor (FIG. 3A) and outside of a theoretical circular or symmetric effective ablation zone centered on the microwave antenna, produces a well-defined ablation region (thick band, as seen in FIG. 3B), extending the region of complete ablation to or beyond the tumor boundary. The study was further designed to test the notion that the thermal accelerant can help avoid the heat loss (also known as "heat sink") caused by a blood vessel adjacent to the ablation zone, without ablating the blood vessel itself This situation is illustrated in FIG. 4, which identifies where to place the thermal accelerant to enhance tumor ablation while avoiding damage to the vessel. FIG. 5 illustrates placement of thermal accelerant and multiple microwave antennas to create a wider and taller ablation region of uniform intensity, showing that if multiple antennae and thermal accelerant are strategically placed, the ablation zone can be expanded. This is to demonstrate a cooperative and synergistic role that the thermal accelerant (TA) plays in augmenting the heating by microwave energy.

FIGS. 3A and 3B schematically diagram the microwave ablation, wherein a thermal accelerant is injected to an imaginary tumor target area. A typical ablation zone is about 2.5 cm in diameter when a single antenna is used with the microwave ablation conditions: 915 MHz, 60 W for 10 minutes. The thermal accelerant, due to its viscous composition, remains relatively stationary at a target site once deposited since it turns to a gel at body temperature. The track of the thermal accelerant gel is shown just outside of the nominal ablation zone, and runs through the outer-boundary of the imaginary tumor in the liver. FIG. 3B shows the coagulative ablation zone extended by augmentation of the microwave energy.

FIG. 4 shows an experimental set-up wherein the thermal accelerant deposited between a major blood vessel (>4 mm in diameter) and the ablation zone to see if the heat loss will be minimized. Because the microwave energy is augmented between the antenna and the thermal accelerant, shorter antenna actuation can achieve complete ablation of the tumor, and the blood vessel itself will be protected from being ablated.

FIG. 5 shows multiple antennae and bodies of thermal accelerant strategically placed to maximize an ablation zone. When two antennae are placed 2 cm apart (d=2 cm) and the two thermal accelerants are placed 2 cm from each antenna to form a rhombus (in cross-sectional view), application of the microwave energy (illustratively total 120 W, 60 W each antenna) for 10 minutes will result in the larger ablation zone than control (d=2 cm, MW only) and a known case of d=1.5 cm (i.e., 915 MHz, 60 W each, 10 minutes, Dmax=3.5 cm, and Dmin=3.3 cm). This demonstrates a cooperative and synergistic role of TA in augmentation of the microwave energy.

A brief discussion of the Thermal Accelerant and the underlying technical considerations may be useful for understanding the scope of materials and effects of the invention and improvements in microwave ablation technology.

The novel MWA methodology is intended to achieve the complete ablation of tumors. The methodology utilizes a thermal accelerant which in one embodiment is comprised of cesium chloride (CsCl) and a reverse phase transition polymer with the following rationale: Tissue ablation by MW energy primarily operates by kinetically exciting water molecules to generate heat. A water molecule is structurally bent (104.5° C.) due to two non-bonding electrons on oxygen atom, and thus has a relatively high dipole moment (1.85 D, D=Debye). At the MW frequency region (300 MHz-30 GHz), water molecules synchronize to the alternating electrical field to cause collisions among themselves, and this energy is converted into heat. Most of alkali and alkaline earth metal ions tend to have high dipole moments (D>7-8, e.g., KBr 10.4 D, BaO 7.9 D), suggesting that these compounds can generate heat more effectively than water molecules. Among these ionic compounds, cesium chloride (CsCl) is particularly interesting not only because of its high dipole moment (10.4 D), but because of its unique physico-chemical and toxicological properties that it offers for MW ablation: First, CsCl is highly soluble in water (1,865 kg/L at 20° C. and 2.7 kg/L at 100° C.). This means that a highly concentrated CsCl thermal accelerant solution can be made if necessary; second, with its high atomic number and density (Z=55 and d=3.99 g/mL), the Cs ion can provide an excellent contrast in CT. This is particularly useful for our purpose since CsCl can be used as a substrate for image-guidance; thirdly, CsCl is non-toxic (LD50=2,600 mg/kg, oral, 910 mg/kg iv, rat). The polymer component possesses the unique property of being a liquid at ambient temperature, but a gel at typical body temperature (35-37° C.). Moreover, upon a further increase in temperature, the polymer precipitates by expelling water molecules from the polymeric lattice structure. The polymer is considered safe, and consists of polyethylene glycol (PEG) that is esterified by a FDA approved poly-(lactic-co-glycolic) acid (PLGA) on both ends. The polymer is biodegradable and biocompatible. CsCl is an ionic compound and, thus, miscible with the aqueous polymer solution to give homogeneous distribution of CsCl permitting uniform heating within the target ablation space. In response to the delivery of microwave energy, CsCl tumbles synchronously to the alternating electric field fueled by its intrinsic dipole moment to generate heat.

Using CT for image guidance, the desired amount of the thermal accelerant with known CsCl concentration can be deposited in the boundary of the tumor mass. Subsequently, the injected heat substrate turns into a gel of predetermined ablation shape and volume. The heat substrate gel will be heated by MW energy transmitted through an MW antenna (MicrothermX® Perseon Medical, Salt Lake City, Utah) to reach tumoricidal temperature (>60° C.) in the targeted area.

Example 2

Preliminary Study: Augmentation of Microwave Energy

Figures 6A, 6B:
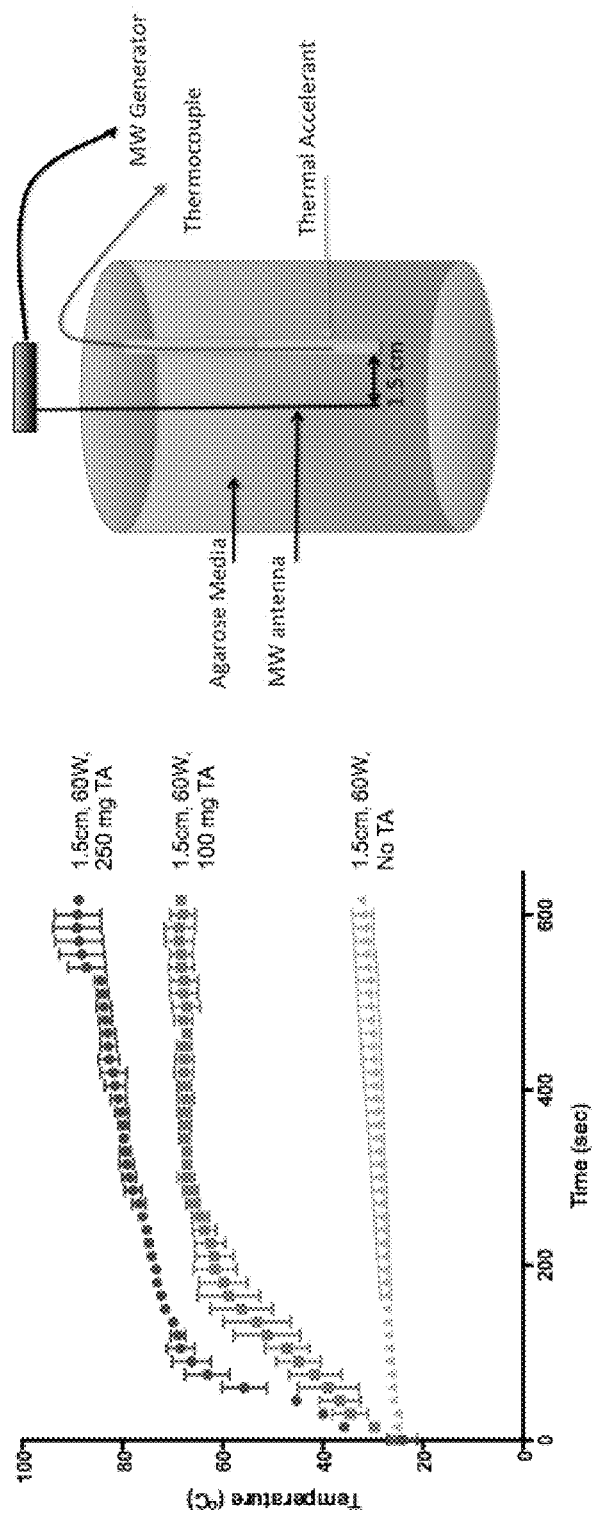
FIG. 6A shows an experimental setup used to evaluate heat augmentation of a thermal accelerant.
FIG. 6B is a Time/Temperature chart of heating for different amounts of the accelerant.

As a proof of concept, we tested the efficiency of the heat substrate in augmenting the microwave energy. Using a phantom (1% (w/v) agarose medium), temperature increase by a control and the heat substrate (two concentrations: 100 mg/mL and 250 mg/mL, respectively) was measured over time. Under the MW conditions (60 W, 915 MHz, 10 minutes), a maximum ablation zone attained is typically 2.5 cm in diameter (i.e., a zone extending a distance 1.25 cm from the antenna). This distance and the conditions were used as a baseline platform to evaluate the augmentation efficiency of the heat substrate. As depicted in FIG. 6B the heat substrate was placed at 1.5 cm from the antenna, and was heated by MW energy transferred through an MW antenna (MicrothermX® Perseon Medical, Salt Lake City, Utah) to reach tumoricidal temperature (>60° C.). Temperature plots are shown in FIG. 6A. The thermal accelerant was found to augment the MW energy in a concentration dependent manner and reached beyond 60° C. within 5 minutes (c. 1 minute 250 mg/mL; <3 minutes 100 mg/mL, respectively) in comparison to the sample without the thermal accelerant. FIG. 6A shows a typical set up for the in vitro experiment.

Example 3

A preliminary study of the thermal accelerant as a CT contrast agent was carried out. Various concentrations of the thermal accelerant (TA) solutions were prepared and measured for their CT contrast. FIG. 2C shows the TA solution with the concentration as low as 10 mg/mL produced a discernable contrast as compared to water. The degree of the CT contrast was found to be proportional to the concentration of the thermal accelerant (TA), so the TA solution is CT visible. The upper portion of FIG. 2C shows four samples 1)-4) as follows: 1. Distilled water −15 Hu, 2. TA (10 mg/mL) 286 Hu, 3. TA (100 mg/mL) 2056 Hu, 4. TA (1000 mg/mL) 3070 Hu. The lower portion of FIG. 2C shows the same samples with computer-aided enhancement. The lowest concentration 10 mg/mL TA yields a discernible contrast compared to water in CT. GE Optima 580 W CT scanner. Used CT protocol: 120 kV, 50 mA, 0.8 second rotation, 0.562:1 pitch, and 16.times.625 mm detector configuration. Radiation output (CTDIvol) was 12.08 mGy. Dose Length Product was 193.88 mGy-cm.

Example 4

Reverse Phase Transition Polymer.

The polymer used with the thermal accelerant desirably has the property of being a liquid at ambient temperature, but a gel at typical body temperature (35-37° C.), which, in some embodiments, can allow the gel to remain stationary at a target site once deposited. Upon a further increase in temperature, the polymer precipitates by expelling water molecules from the polymeric lattice structure as shown in FIG. 2D supra. The polymer of this example is technically a block-co-polymer that is made of poly(lactic-co-glycolic acid) (PLGA) and polyethyleneglycol (PEG). PLGA is a FDA approved polymer for its biocompatibility like PEG. The polymer used as a heat substrate component here is structurally arranged as follows: PLGA-PEG-PLGA. At ambient temperature (25° C.), the polymer is conformed in such a way that a PLGA interacts with the intramolecular PLGA to form a hairpin. This conformation will change as the temperature increases so that intermolecular PLGA-PLGA interactions predominate (37° C.). Upon further heating (>60° C.), the conformation will be changed back to the hairpin conformation except that water molecules are expelled out of the polymer layer at higher temperature.

Example 5

Ex Vivo Experiment Augmentation of MW Heating by the Heat Substrate in a Whole Calf Liver.

A whole calf liver was heated with MW energy 60 W, 915 MHz: A small volume (350 µL) of 100 mg CsCl in 20% (w/v) polymer solution was injected to a point 1.5 cm away from the tip of the MW antenna. After 10 minutes, the area was cut open to observe the polymer solution transformed into a precipitate. The temperature was plotted showing the temperature increase to be proportional to the TA concentration. At 250 mg/mL, the temperature reached 60° C. within 3 minutes. At 100 mg/mL, it took approximately 5 minutes, while without TA the temperature increase was nominal.

Figure 7:
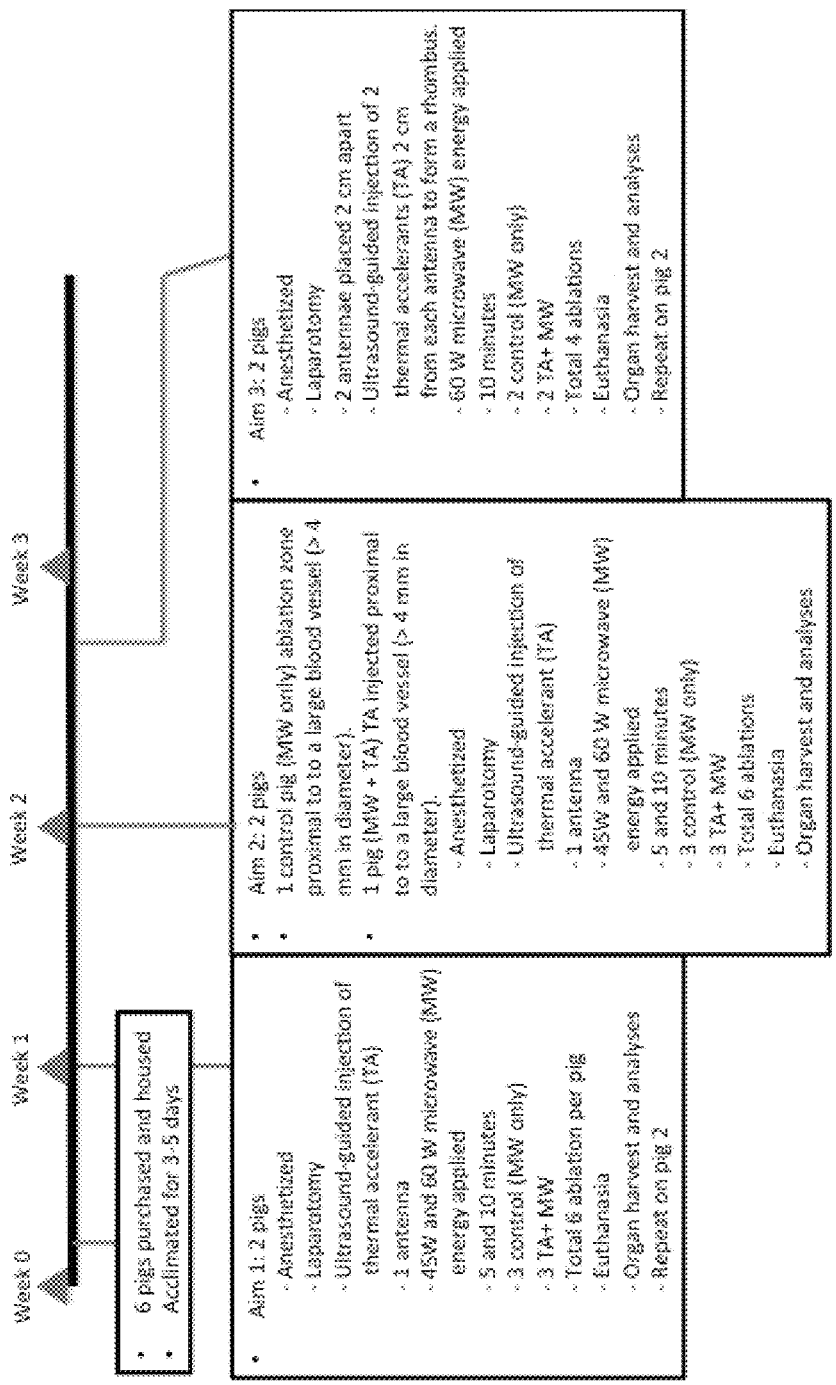
FIG. 7 is a chart of an investigational in vivo animal protocol designed to identify effective ablation materials, parameters and operating procedures.

The foregoing observations and measurements provided substantial confirmation of the underlying concepts, and further motivation to pursue in vivo animal investigations which could identify the magnitudes of any effects due to live-subject tissue conditions, such as perfusion effects or corrections for blood flow in a vessel, and establish variances in ablative results. In such a study a pilot study) would have as Specific Aims one or more of the following: Aim 1) Laparotomy will be performed on a pig, and the liver will be exposed. Using ultrasound as image-guidance, the microwave (MW) antenna will be inserted and the microwave energy of the preset parameters will be applied. Similarly, the thermal accelerator (TA, 250 CsCl mg/mL of 20% (w/v) polymer solution) is injected to the liver parenchyma, an imaginary target area using ultrasound as image-guidance and deposited as a stationary gel. The MW antenna will be inserted approximately 1.5 cm away from the thermal accelerant. The microwave energy of the same parameters will be applied to the antenna (i.e., 915 MHz, 45 or 60 W for 5 to 10 minutes). All animals will be euthanized immediately after the procedure, and the liver will be harvested for further comparisons including CT and analysis of the ablation patterns and measurement of the ablation volume; Aim 2) As described in Aim 1), the animals are anesthetized and laparotomized to expose the liver. With ultrasound guidance, the antenna will be placed 1.5 cm from a large blood vessel and ablated with the preset conditions (915 MHz, 45 or 60 W for 5 to 10 minutes) on the first pig (control). In the second pig's liver, the antenna will be placed 1.5 cm from a large blood vessel after the thermal accelerator is injected near the blood vessel, and then the microwave energy is applied. Each pig will receive three ablations: 1) 45 W for 10 minutes, 2) 60 W for 5 minutes, 3) 60 W for 10 minutes. Immediately after the procedure is complete, the pigs are euthanized to harvest the liver for CT and analysis of the ablation patterns and measurement of the ablation volume by depth, height, and width; Aim 3) A pig liver will be exposed after laparotomy is performed on a pig under anesthesia. Using ultrasound as image-guidance, two antennae will be inserted in the liver 2 cm apart and the microwave energy (60 W) will be applied for 10 minutes for control. In the same liver, two antennae will be inserted 2 cm apart, and followed by two injections of the thermal accelerant (TA) by which the injection is made 2 cm away from each antenna to form a rhombic shape as depicted in FIG. 3. The microwave ablation will be performed under the same conditions as control (i.e., 60 W, 10 minutes). After the procedure is complete, the pigs are euthanized to harvest the liver for CT and analysis of the ablation patterns and measurement of the ablation volume by depth, height and width. FIG. 7 is a chart showing a proposed investigative protocol.

Briefly, the Aim 1 is intended to examine heat augmentation efficiency of the thermal accelerant (TA) in percutaneous microwave ablation using a single antenna, while Aim 2 is intended to assess efficacy for overcoming heat sink effects, and Aim 3 investigate the TA being used for situations that may have been addressed previously by using an extra antenna.

As described above, the thermal accelerant was conceived in order to mitigate the incomplete ablation issue, and envisions a novel thermal accelerant (TA) that can augment the microwave energy from a distance unreachable by a single antenna alone. This helps not only extending the ablation zone covering the outer-boundary of a tumor mass but also ablating more rapidly. As clinically shown, more effective and faster microwave ablation helps the procedure be more complete, thus lowering rate of tumor recurrence rate. In addition, TA can be injected strategically near a heat sink so that the heat loss can be prevented.

The TA, for best utility in image-guided thermal ablation to treat tumor, preferably has the following properties: 1) it can augment the electromagnetic radiation energy (e.g., radiofrequency, microwave), especially from a distance unattainable by a single antenna; 2) it is visible under various imaging modalities (e.g., computed tomography (CT), ultrasound or MM); 3) it is injectable, and is stationary once injected, e.g., due to its viscous composition; and 4) it is non-toxic.

As described above, a synthetic polymer with an alkali rare earth salt (CsCl) has been found useful, however other polymer materials such as albumin, DNA, RNA, or glycoproteins and/or glycopolymers, such as IgA, IgG, IgM, and other immunoglobulins offer similar benefits, and the viscosity properties and other traits of albumin or similar preparation can be further tailored by concentration, salt content and other steps. Generally, the components of the TA may include three, non-toxic components: 1) a polymer (natural or artificial) as a carrier; 2) an ionic component for overall charge and viscosity balance; 3) an imaging component. With the optimal compositions of the three components, TA can be deposited at the target area of the tumor under image-guidance (e.g., US, CT or MRI), and be able to augment the applied energy (e.g., microwave, radiofrequency or electroporation) to better achieve complete ablation. For example, TA comprised of bovine serum albumin (BSA), NaCl and tantalum powder satisfy the aforementioned criteria, to provide more effective ablation resulting in elimination of untreated outer-boundary of tumors and the heat sink effect. The salt adjusts the charge distribution within the albumin, while tantalum enhances its imaging characteristics. For magnetic resonance imaging the preparation demonstrates signal decay rate time constants ($T_1$) shorter than many tissues. As an example, liver at 3 Tesla has $T_1$ of approximately 800 ms. The albumin/NaCl preparation has $T_1$ in the range of 250 ms to 330 ms, depending on the concentration of NaCl. In a $T_1$-weighted MRI scan for image guidance, the TA will show substantially brighter than surrounding tissue (positive contrast) allowing for unambiguous positioning of the material. $T_2$ contrast mechanisms can also be used, primarily via negative contrast in which the TA has shorter $T_2$ than surrounding tissue and $T_2$-weighted scans are used for guidance.

Albumins belong to a globular protein family, which are water-soluble, moderately soluble in concentrated salt solutions, and experience heat denaturation. Albumins are commonly found in blood plasma and differ from other blood proteins in that they are not glycosylated. A number of blood transport proteins are evolutionarily related, including serum albumin, alpha-fetoprotein, vitamin D-binding protein and afamin. Serum albumin is the most abundant of human blood plasma. It binds water, cations (E.g., Ca2+, Na+ and K+), fatty acids, hormones, bilirubin, thyroxine and pharmaceuticals (including barbiturates and taxol). Its main function is to regulate the colloidal osmotic pressure of blood. The isoelectric point of albumin is 4.9 (of human serum albumin, Ip=4.7).

Albumin is comprised of 3 domains of similar structure, which all originated from the same domain. Each domain is composed of ten α-helices and can be further divided into two subdomains, denoted as A and B, containing 6 and 4 helices, respectively. The two subdomains are connected by a long amino acid loop, which is responsible for the change in orientation of the subdomains. On the other hand, the conformational flexibility between domains depends on the bending of the helices. Its canonical structure is supported by a conserved set of 17 disulfide bridges, which are maintained in all mammalian serum albumins. Of the 3 domains, the first domain is the only one to contain 5, not 6, disulfide bridges, missing one at Cys-34. Instead, the lack of an intramolecular disulfide bridge forming at Cys-34 allows albumin to dimerize with another albumin molecule at this residue. HSA, BSA, LSA, and ESA have exchanged 70-85% of their residues over the course of 500 million years, however the positions of the cysteines and disulfide bridges have not changed. Additionally, although the domains have undergone significant evolutionary changes, their overall architecture and secondary structure elements have remained unchanged.

As shown in the above-described examples, microwave ablation with the TA can produce significantly larger ablation volumes than that of the control in porcine liver, lung, kidney, and muscle. In some embodiments, the TA can be controlled to "switch-off" at specific temperatures during ablation to control the ablated volume. As the main component of the Thermal Accelerant (TA), a water-soluble protein (e.g., albumin) can be used in the ambient and physiological temperature range. The protein component can be coagulated as temperature increases at which the ability to augment the energy of TA ceases since the conformation of the protein is altered. The coagulation temperature is pH-dependent, i.e., low pH shifts the coagulation (denaturation) temperature of albumin from 62° C. (at pH 7.4) to 46° C. (at pH 3.5). Such ability to control the TA can allow for protection from collateral injury of important tissues or organs during ablation. While it will be appreciated that the temperature at which the TA switches off can be varied, though some non-limiting examples of such temperatures can be >60° C., >80° C., >100° C., and so forth in optimized formulations, in some embodiments, temperatures of up to 170° C. can be observed under in vitro conditions during microwave ablations under the following conditions: 915 MHz, 60 W for 10 minutes at 1.5 cm from the antenna. For example, under these ablation conditions, e.g., 915 MHz, 60 W, 10 minutes, using an (2 mL) injection of TA (HeatSYNC Gel) 1.5 cm from the antenna, using the Perseon MW system (Perseon Medical, Salt Lake City, Utah), ablation volumes that were larger than ablations without TA were produced for each of the four tissue types, with superior reproducibility, as demonstrated in Table 2, reproduced below:

|  | Ablation conditions | | | | Ablation Results | | |
| --- | --- | --- | --- | --- | --- | --- | --- |
| Tissue | Frequency, power (MHz, W) | Duration of ablation (min) | Distance between antenna and TA (cm) | Types of TA | Ablation Volume with TA ($cm^3$) | Ablation Volume of Control ($cm^3$) | p |
| Liver[A] | 915, 60 | 10 | 1.5 | HeatSYNC Gel | 6.80 ± 0.62 | 2.69 ± 0.36 | <0.01 |
| Lung[B] 9, 10 | 915, 60 | 10 | concentric | HeatSYNC Gel | 4.6 ± 1.9 (PC 5.6 ± 1.8) EB 3.4 ± 0.4 | 1.9 ± 0.9 | <0.01 EB <0.01 |
| Kidney[C] | 915, 60 | 10 | 1.5 | BSA-based TA | 12.6 ± 0.97 | 4.69 ± 1.98 | <0.01 |
| Muscle[D] | 2450, 100 | 10 | 1.5 | HeatSYNC Gel | 41.9 ± 4.2 | 28.7 ± 10.2 | <0.01 |

Ablation was performed on a plurality of samples of organs (A-D), with each multiple samples being exposed to TA and multiple samples acting as the controls. As shown in Table 2, ablation volumes with TA for certain tissues were, in some instances, almost three times greater than those of the control in which TA was not used.

Figures 8A, 8B:
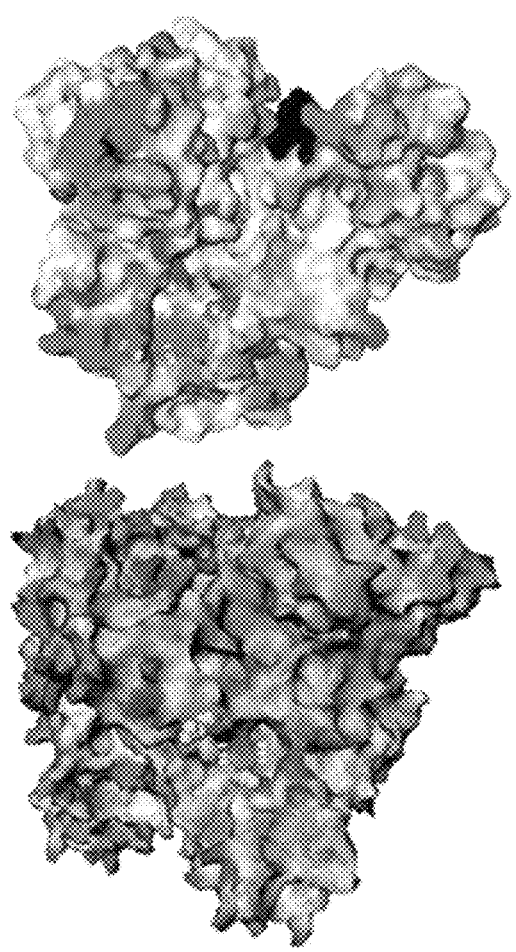
FIGS. 8A and 8B illustrate the surface potential of HSA and of BSA, respectively, with areas of positive and negative charge shaded or colored differently.

FIG. 8A and FIG. 8B illustrate the surface potential of HSA (A) and BSA (B), with different colors representing positively and negatively charged areas. Vincent Goovaerts et al., Phys. Chem. Chem. Phys., 2013, 15, 18378-18387. Mature BSA contains 583 amino acids and has 99 positive (K, H, R) and negative (D, E) residues. Similarly, mature HSA contains 585 amino acids and has 99 positive (K, H, R) and 98 negative (D, E) residues. Although the general structure of the protein is conserved among mammalian serum albumins, there are significant differences. In sequence, BSA shares only 75.8% homology with HSA. Their structures are canonical (due to the conserved disulfide bridges), but differ in surface amino acids. As a result, the ligand binding pockets in the various serum albumins show different amino acid compositions and slightly different conformations, allowing for the binding of different ligands.

The tantalum component of TA is a high radiopaque material that provides fluoroscopic visualization. Tantalum is an inert metal with a history of use in implants requiring incorporation of a contrast agent, such as arterial stents, hip prostheses, and embolization materials. [9, 10] In addition to its use in embolization materials, tantalum powder has been used as a contrast agent injected into the cervical spinal cord for visualization during percutaneous cordotomy. Additionally, tantalum powder has found uses in neurosurgery, to mark the plane of section in lobotomy or leucotomy, to provide visualization or definition of a site for tumor removal, and for detection of recurrent subdural hematoma after surgery.

Although the properties of serum albumin have been extensively studied under physiological conditions studies on the highly concentrated albumins (i.e., 300 mg/mL), especially, as a carrier of an imaging contrast agent or a thermal accelerant are rare. Nonetheless, calculated dipole moment of serum albumin in vacuum is very large, 710 D (D=Debye) in comparison to the TA substance first-described above, CsCl (ca. 10 D) or compared to water (1.85 D). Despite its large dipole moment, physiologically available bovine serum albumin (BSA) alone does not increase the temperature rapidly due to its low dielectric constant and the loss factor in the range of frequencies of interest, i.e., 915 MHz-2.45 GHz. [12] With 500 mg/mL BSA, a gradual increase to 40-50° C. was observed in vitro at 10 min for 60 W with a 915 MHz when the antenna was positioned a distance of 1.5 cm from the BSA sample. The temperature increase was insufficient to make BSA alone as a TA. It will be appreciated that in some embodiments, the calculated dipole moment of a carrier can be up to, and including, 1,000 D.

Figure 9:
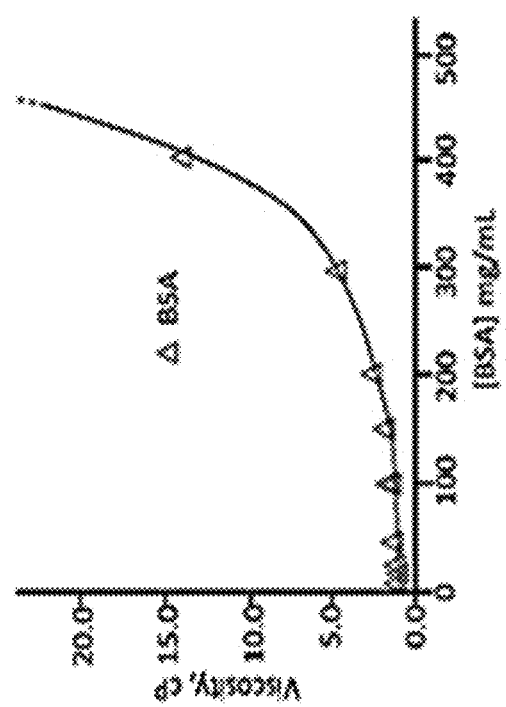
FIG. 9 shows the viscosity of BSA as a function of its concentration in mg/mL.

Furthermore, the albumins of high concentrations (>300 mg/mL) tend to have a very high viscosity due, in most part, to protein-protein interactions as shown in FIG. 9 which schematically illustrates the viscosity of BSA as a function of concentration. For example, in some embodiments the viscosity of the TA can depend on the formulation, but in some embodiments, can range from approximately 50 centiPoise to approximately 25,000 centiPoise. Relative examples of viscosity of compounds are shown in Table 1 below:

| Compound | Viscosity (cP) |
| --- | --- |
| Motor Oil SAE 10 or Corn Syrup | 50-100 |
| Motor Oil SAE 30 or Maple Syrup | 150-200 |
| Motor Oil SAE 40 or Castor Oil | 250-500 |
| Motor Oil SAE 60 or Glycerin | 1,000-2,000 |
| Karo Corn Syrup or Honey | 2,000-3,000 |
| Blackstrap Molasses | 5,000-10,000 |
| Hershey's Chocolate Syrup | 10,000-25,000 |

Materials or formulations with a high dipole moment as potential thermal accelerants can be expressed by the $\varepsilon''$ and $\sigma$ values for thermal ablation (radiofrequency, microwave, irreversible electroporation. A person skilled in the art will recognize that in order to show the capacity of a material, or formulations of a material, quantitatively as a thermal accelerant, the concept of permittivity can be employed in lieu of, or in addition to, evaluation of dipole moment. For example, materials can be tested using an electromagnetic wave of sinusoidal frequency $\omega$, which is directed at a subject sample by an open-ended coaxial cable of a low-power oscillator. Measurement of the magnitude and phase of the fraction of the wave which is reflected allows deduction of the complex permittivity of the tissue. Table 2 illustrates dielectric constant ($\varepsilon'$), loss factor ($\varepsilon''$), and electrical conductivity ($\sigma$) of various materials for use in the thermal accelerant at 915 and 2450 MHz:

|  | 915 (MHz) | | | 2450 (MHz) | | |
| --- | --- | --- | --- | --- | --- | --- |
| Material | ε' | ε" | σ | ε' | ε" | σ |
| Water | 78.3 | −0.403 | 0 | 76.9 | −9.23 | 0.1 |
| MeOH | 31.2 | −8.81 | 0.1 | 22.2 | −11.7 | 0.1 |
| 1% NaCl | ~70 | −20 | 1.1 | ~70 | −27 | ~1.5 |
| albumin | 30.7 | −10.2 | 0.52 | 37.9 | −8.20 | 1.12 |
| TA-4 | 40.15 | −93.16 | 4.74 | 32.25 | −50.7 | 5.79 | wherein complex permittivity is defined as $\varepsilon^* = \varepsilon' - j\varepsilon''$, where $\varepsilon'$ is the real permittivity and $\varepsilon''$ is the imaginary permittivity. Both quantities are dimensionless numbers expressed as a multiple of the permittivity of free space, $\varepsilon_0 = 8.854 \times 10^{-12}$ farad/meter. The real permittivity is also known as the dielectric constant. The imaginary permittivity is also called the loss factor and can be written $\varepsilon'' = \sigma/(\omega\varepsilon_0)$, so as to incorporate the electrical conductivity of the material, $\sigma$. The quantity $\sigma$ directly scales the power deposited per unit volume according to the following expression, $ARD = \sigma|E|^2$, where ARD is Absorption Rate Density (watt m$^{-3}$), $\sigma$ is electrical conductivity (ohm$^{-1}$ m$^{-1}$), and $|E|$ is the magnitude of the electrical field (volt m$^{-1}$) produced by the microwave antenna at the point of interest in the tissue.

As shown in Table 2 above, the electrical conductivity, $\sigma$, at 915 MHz of one sample (TA-4) equal to 4.74 mho/m with real permittivity ($\varepsilon'$, 40.147) and imaginary permittivity ($\varepsilon''$, −93.164). Albumin contains (ca. 66 kDa) with roughly 200 ionic residues (100 positive and 100 negative). These residues are arranged in 3-D to have its overall polarity (dipole moment) of approximately 700 D (Debye). However, the key parameters ($\sigma$, $\varepsilon'$, $\varepsilon''$) are similar to those of MeOH due to the protein-protein interaction forces within the solution. In order to break these forces apart, a chaotrope such as NaCl or sodium citrate can be used, as discussed above. For example, sodium citrate can be used as a chaotrope for human serum albumin, though it will be appreciated that, in some embodiments, additional chaotropes can be used. The chaotrope can be used to break apart the protein-protein interactions of molecules to allow the molecules to move more freely to generate more heat. It will be appreciated that while some chaotropes can be ionic so as to be a part of the ionic component of the TA, in some embodiments, the chaotropes can be non-ionic or slightly ionic such that the chaotropes are miscible in aqueous solutions.

The effect of the chaotrope can increase $\sigma$, and $\varepsilon''$ values, as shown in the table, values that can be approximately 4.2 times greater than the value for normal saline solution, which is typical of living tissue. This large-scale factor directly expresses the increase in heating rate above that which would be present without the injection of TA into the tumor. That is, electrical conductivity $\sigma$ and loss factor $\varepsilon''$, namely that the loss factor $\varepsilon''$ increases with the ionic concentration, which thereby increases tissue conductivity for alternating electrical current in the frequency of radiowaves can be used to explain both microwave and radiofrequency ablation. Some non-limiting examples of chaotropes can include L-glycine, L-alanine, L-valine, L-proline, L-serine, L-histidine, L-arginine-HCl, L-histidine-HCl, L-lysine-HCl, L-glutamic sodium, urea, and NaAc.

The values in Table 2 above illustrate the effect of the chaotrope on dielectric properties of various materials. For example, albumin and TA-4 have similar values of real permittivity, 30.7 and 41.15, respectively, while the respective values of loss factor jump from −10.2 to −93.16, which is greater than a nine-fold increase. By way of further example, TA-4 has an even greater increase in the loss factor when compared to methanol, which has a loss factor value of −8.81, which is similar to that of albumin. Methanol and albumin alone are therefore much less effective as thermal accelerators as compared to when a chaotrope is added. Compounds such as albumin tend to be highly concentrated, having little water between ionic components within the albumin molecule. As a result of this high concentration, the distance between albumin molecules is reduced, causing the positive and negative charges between the molecules to interact, which results in restricting mobility of each albumin molecule under oscillating RF or microwave. Adding a chaotrope, such as NaCl, can break apart the protein-protein interactions between the albumin molecules to allow each albumin molecule to freely move, thereby increasing friction and kinetic energy of the molecules causing the molecules to tumble, which is then transformed into heat energy for larger increases in temperature.

It will be appreciated that the effects of chaotropes can be affected by other properties of materials. For example, for 1% NaCl, as described in Table 2 above, addition of the chaotrope can increase the temperature of the 1% NaCl due to its high dipole moment, though the temperature increase will be smaller as compared to albumin due to the smaller size of the NaCl molecule. One skilled in the art will appreciate that the tumbling motion of the larger albumin molecules generate more kinetic energy as compared to the smaller NaCl molecules, which can account for the larger increases in heat of the albumin molecules.

Figure 10B:
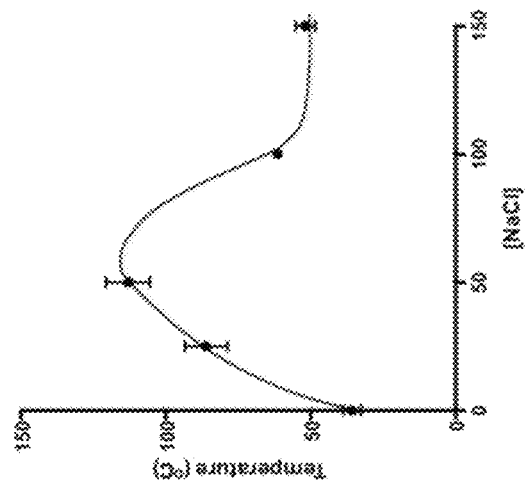
FIG. 10B shows the end-temperature increase at 120 seconds as a function of the NaCl concentration
Figure 10A:
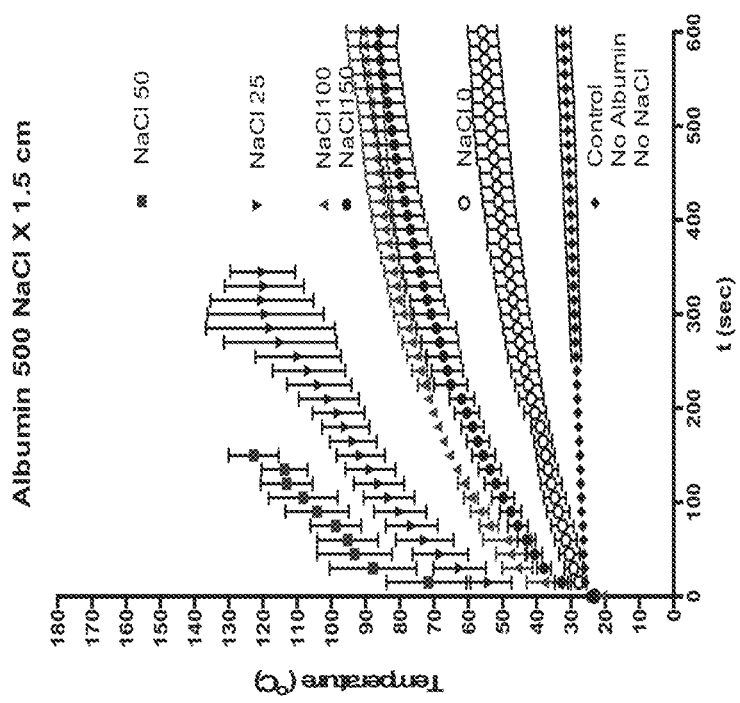
FIG. 10A shows temperature increase over time of a control and of albumin thermal accelerant (TA) having different amounts of NaCl positioned 1.5 cm from a microwave antenna.

Under the applied microwave radiation, the surface charges of the albumin molecule are occupied by the intermolecular interactions with the readily available other albumin molecules. In order to relieve the interactions, we used NaCl as a chaotrope. In essence, it is believed that the intermolecular interactions of BSA molecules consist of charge-charge, dipole-dipole as well as hydrophobic interactions, and thus exhibit high viscosity. By adding NaCl to the solution, the viscosity will be lowered by the salt ions competing with other BSA charges and subsequent solvation by water molecules. This will free up the individual BSA molecules to respond to the microwave energy. We have examined the effect of [NaCl] on thermal acceleration efficiency of the albumin (500 mg/mL), and the results are shown in FIG. 10A. The concentration of NaCl inducing the optimal TA efficiency is slightly higher than 50 mg/mL but less than 75 mg/mL. The higher concentrations suppress the efficiency (>75 mg/mL NaCl), and has a solubility limit beyond 230 mg/mL. FIG. 10A shows the effect of various NaCl concentrations on microwave ablation (MWA, 60 W, 915 MHz, 10 minutes, distance from the antenna=1.5 cm). FIG. 10B is a schematic plot of temperature v. [NaCl] concentration at the 120 second endpoint under the same microwave regimen, showing a temperature peak at around 50 mg/mL NaCl.

Albumin thermal accelerant as described above was used in a number of in vivo microwave ablation experiments in pigs and the ablated sites were stained with triphenyl tetrazolium chloride to distinguish dead from viable cells. The images from these further experiments demonstrated that MWA with TA yields a larger ablation zone than control using a typical microwave ablation (915 MHz, 60 W, 10 minutes d=1.5 cm) without TA as a control. Under the same MWA conditions, TA (1 mL of albumin (500 mg), NaCl (50 mg)) generated a larger ablation zone unaffected by a large blood vessel (1 cm in diameter). A MWA was performed on the left medial lobe of the swine liver (915 MHz, 60 W, 10 minutes d=1.5 cm). Under the same MWA conditions with TA (1 mL of albumin (500 mg), NaCl (50 mg)) generated a larger ablation zone on the same lobe of the liver. A MWA on the left medial lobe of the swine liver (915 MHz, 60 W, 10 minutes, d=1.5 cm) was compared to a MWA with TA (1 mL of albumin (500 mg), NaCl (50 mg) injected behind the blood vessel. For that procedure the ablation zone was seen to extend through the blood vessel (>4 mm in diameter) completely surrounding the blood vessel. In tandem with the previous example, this demonstrated that MWA with TA is able not only able to augment the microwave energy but also to block the heat loss caused by the "heat sink" effect. In an additional experiment, an ultrasound image was taken immediately after ablation was complete (10 minutes), with the blood vessel positioned in between the antenna and TA. During the ablation, blood flow in the vessel was seen to be normal, which indicates that the microwave energy was able to penetrate through the functioning blood vessel and operate effectively in the far field without overheating the vessel. This suggests that the "heat sink" effect can be eliminated by the ablation methodology. Other TTC-treated kidney tissue images show a typical ablation zone using a single antenna with 60 W, 915 MHz, for 10 minutes, and the ablation is slightly off-centered as the connective tissues in the central renal sinus area are less affected. The resultant ablation zone is about 1 cm in diameter. TA was able to produce a drastic increase of the ablation zone (3 cm in diameter) where the central tissues were also shown to be completely ablated (60 W, 915 MHz, 10 minutes; the distance between antenna and TA was 1.3 cm).

Figure 11:
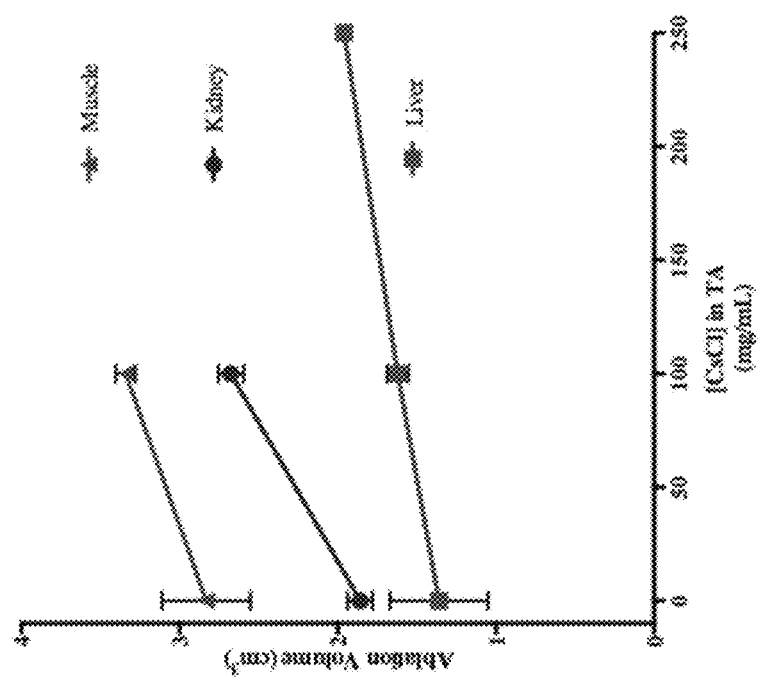
FIG. 11 shows increased ablation volumes achieved in different tissues using different concentrations of a Cesium Chloride component.

FIG. 11 show the results of further tissue ablation experiments done to assess ablation volumes in cm.sup.3 for 1 mL of the thermal accelerant in different tissues (kidney, muscle and liver) with no TA or 1 mL of the TA at different concentrations of CsCl absorber. In each case the effective ablation zone was greater with the TA. Different concentrations of TA were tested with concentrations up to 250 mg/mL for the liver tissue ablation, as the liver is a key organ for treatment by this method. The other tissues also showed significant ablation volume increases.

As described above, the heat substrate or thermal accelerant of the present invention can be implemented in various forms or concoctions, and may involve tailoring the physical characteristics of a natural or artificial polymer to improve their utility as injectable, fixable, imageable and heatable media. Several strong initial materials have been described, but simple testing can quickly reveal or confirm additional ones. Thus, in addition to or in place of the cesium chloride microwave accelerant, other halides such as the bromide or iodide, and other alkaline or alkaline earth cations that are medically useful may be expected to offer similar if not comparable ablation enhancement. For example Rubidium chloride, or a suitably protected rubidium portion may be useful. Similarly, in addition to BSA and PLGA-PEG-PLGA polymers, materials in alginate media, or salts having anions such as carboxylate or sulfite materials may be employed if they exhibit suitable characteristics, and a discussion of useful cations, anions or electrolyte or other materials for optimizing the desired physical imaging, heating and other characteristics of the thermal accelerant are included above. By way of example, various embolization media can be so modified, and their basic emulsion-like composition will also provide ultrasound imageability. Further, formulation of albumin with sodium chloride salt has been shown to provide a low-viscosity thermal accelerant having appropriate physical characteristics for diverse tissue treatments (including intravascular) with good microwave heating performance, while being completely biocompatible. Different ones of the described thermal accelerants may be appropriate for different microwave regimens of 400 MHz, 915 MHz, 2450 MHz, or 5800 MHz range, and may be used if they are medically safe and result in effective microwave ablation enhancement characteristics for the tissue, tumor mass or organ under consideration.

In addition, the described polymer can be delivered to a vessel in the target tissue and heated to act as an embolization substance to block a vessel that feed the target tumor to thereby cause tumor regression by cutting off oxygen and nutrients supply through the vessel. A further variation is to add one or more anticancer drugs or treatment agents to the polymer, so that once localized and heated the polymer serves as an in-situ time-release treatment agent.

The invention described herein involves the ablation methodology of creating thermal lesions by augmentation of the electric or electromagnetic energy, e.g. absorption of radiated energy and conversion into thermal energy. The ablation methodology includes a thermal accelerant (TA) that functions as a satellite energy absorber, e.g., to increase the heating effect. The thermal accelerant (TA) is preferably comprised of three components, 1) polymer (natural or artificial) as a carrier; 2) an ionic component or equivalent for overall charge and viscosity balance; 3) an imaging component which allows the ablation procedure to be monitored.

Other polymers may include either natural or artificial, for example, albumins, silk, wool, chitosan, alginate, pectin, DNA, cellulose, polysialic acids, dendritic polylysine, poly (lactic-co-glycolic) acid (PLGA). The ionic component may include, $M^+X^-$ or $M^{2+}Y^{2-}$, where M belongs to alkaline or alkaline earth metal such as Li, Na, K, Rb, Cs and X represents halogens, acetate and other equivalent counter balance to $M^+$, and Y can be $X_2$ or mixed halogens, acetates, carbonate, sulfate, phosphate and other equivalent counter balance to M.sup.$^{2+}$. Other organic components can independently affect these roles. See: Wang, S. et al, Mol. Pharmaceutics 2015, 12, 4478-4487. For CT imaging, cesium, tantalum, iohexol, ethiodized polymers such as PLGA, PEG, albumin can be utilized, while for ultrasound imaging, polymers have been found to be in general hypoechoic. However when PLGA-PEG-PLGA (a block co-polymer, a reverse phase-transition hydrogel) is used, the polymer appears hypoechoic immediately after injection subsequently turns into hyperechoic as temperature increases. A similar observation was made when albumin is used as a carrier polymer.

Upon application of electromagnetic energy to drive ablation (e.g., microwave, RF, electroporation), remotely deposited TA can absorb the energy much more effectively than the surroundings and help extend the ablation zone. Remotely deposited TA, here means at a distance greater or equal to 1.5 cm from the antenna open slot, when the conditions (60 W 915 MHz for 10 minutes) are used as reported in Appendix C. As described above, upon application of the electromagnetic energy (e.g., microwave, RF, electroporation) TA deposited adjacent to a large blood vessel can prevent the ablation target from suffering excessive heat loss, therefore TA can mitigate the "heat sink" effect to provide complete ablation. In addition, TA can be used in embolization/ablation combination treatments to destroy tumors. TA has a viscosity similar viscosity to Lipiodol, thus can be delivered via an intravascular catheter to be deposited accurately. A subsequent ablation can destroy tumors effectively.

Thus, as an overview and recapitulation, the thermal accelerant (TA) formulations and materials described above can function as satellite energy absorbers to create thermal lesions by augmenting the coupling of the electric or electromagnetic energy into heat at distances not effectively treatable by an antenna alone. The TA may be comprised of three components, 1) polymer (natural or artificial) as a carrier; 2) an ionic component or equivalent for overall charge and/or viscosity balance; and 3) an imaging component. The polymers may include either natural or artificial, for example, albumins, silk, wool, chitosan, alginate, pectin, DNA, cellulose, polysialic acids, dendritic polylysine, poly (lactic-co-glycolic) acid (PLGA), gellan, polysaccharides and poly-aspartic acid, and combinations thereof. The ionic component may include, $M^+X^-$ or $M^{2+}Y^{2-}$ (as a generalized formula $M^{n+}Y^{n+}$) where M belongs to alkaline or alkaline earth metal such as Li, Na, K, Rb, Cs and X represents halides, acetate, and other equivalent counter balance to $M^+$, and Y can be $X_2$ or mixed halides, acetates, carbonate, sulfate, phosphate and other equivalent counter balance to $M^{2+}$ as well as formic acid, glycolic acid, lactic acid, propionic acid, caproic acid, oxalic acid, malic acid, citric acid, benzoic acid, uric acid and their corresponding conjugate bases. Other organic components can independently be substituted as described in Wang, S. et al, Mol. Pharmaceutics 2015, 12, 4478-4487.

For CT imaging, cesium, tantalum, iopamidol, iohexol, ioxilan, iopromide, iodixanol, ioxaglate, diatrizoate, metrizoate, iothalamate, ethiodized polymers such as PLGA, PEG, albumins, DNA, RNA, ionic poly-carbohydrates and the combinations there of can be utilized; For ultrasound imaging, polymers are in general hypoechoic. However, when PLGA-PEG-PLGA (a block co-polymer, a reverse phase-transition hydrogel) is used, the polymer appears hypoechoic immediately after injection but subsequently turns into hyperechoic as temperature increases, indicating likely imageability. A similar observation was made when albumin is used as a carrier polymer.

Upon application of the electromagnetic energy (e.g., microwave, RF, electroporation), remotely deposited TA can absorb the energy much more effectively than the surroundings and help extend the ablation zone. Here, "remotely deposited TA" means in the far range, so would mean distance greater or equal to 1.5 cm from the microwave antenna, for example, when the conditions (e.g., 60 W 915 MHz for 10 minutes) are used. Using TA, the ablation zone can extend further from the antenna for a given power/time treatment, or the same ablation volume can be effectively ablated in a shorter time, or the degree of heating can be enhanced in specific tissue regions that are inherently less capable of microwave heating.

Upon application of the electromagnetic treatment energy (e.g., microwave, RF, electroporation) TA deposited adjacent to a large blood vessel can protect the ablation zone from heat loss, therefore TA can mitigate the "heat sink" effect to assure complete ablation. Moreover, suitably-placed TA may extend ablation to the far side of a vessel, enabling new treatment geometries for simple microwave antennas.

In addition, TA can be used in embolization/ablation combination treatments to destroy tumors. TA may be formulated with a similar viscosity to Lipiodol, and thus can be delivered via an intravascular catheter to be deposited accurately. A subsequent ablation can destroy tumors effectively.

The TA formulation may include excipients, which may depend upon the specific purpose. Excipients may, for example, include, PEG, lactose, microcrystalline cellulose, sodium starch glycolate, croscarmellose sodium, PVP, HPMC, magnesium stearate, colloidal $SiO_2$.

The tissue targets may be quite diverse, and use of TA in the field of Cancer/Tumor ablation may include breast (benign and malignant), thyroid (benign and malignant), lung (primary and metastatic), liver (primary and metastatic, liver surgery margin coagulation), adrenal (benign functioning, cancer and metastatic), kidney (primary and metastatic), bone, prostate, soft tissue (primary and metastatic). In addition, the enhanced ablation accuracy, speed and uniformity offer promising improvements for Endometrial ablation/Menorrhagia: Uterus; Spinal Decompression and Denervation; Benign Prostatic Hyperplasia (BPH); as well as treating other tissues such as Esophagus (reflux), bronchial tree (emphysema reduction), biliary tree (stent obstruction from tumor), joints (laxity), surgical resection and bleeding.

As discussed above, in some embodiments, radiofrequency (RF) can drive ablation in addition to, and/or in lieu of, microwave energy. A person skilled in the art will recognize that RF can use electrical signals (e.g., a current) of varying frequency, e.g., both inside and outside frequencies of radio waves, to perform ablation. Among other ways to perform an RF ablation, needle-like electrodes can be placed percutaneously into the target tissue using imaging guidance (e.g., ultrasound, CT imaging, or MM).

Figure 12:
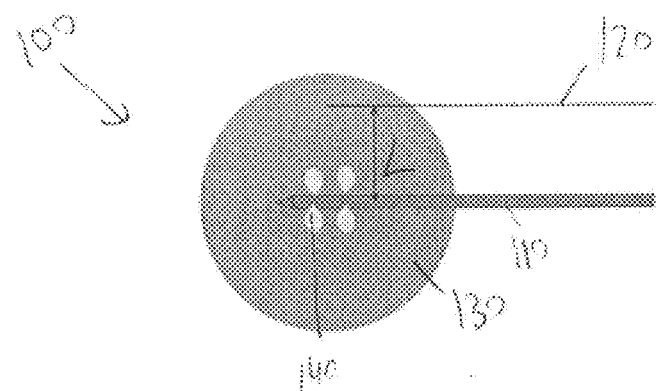
FIG. 12 schematically illustrates an arrangement of an electrode and TA being inserted into an organ of a patient.

FIG. 12 illustrates an exemplary embodiment of a setup 100 used for RF ablation. As shown, a probe, or electrode 110, and a thermocouple 120 can be inserted into tissue or an organ (both identified for simplicity by reference number 130), e.g., heart, liver, kidney, and so forth. A distance L between the probe 110 and the thermocouple 120 can vary, though in some embodiments, the distance L can be approximately 1 cm, approximately 1.5 cm, approximately 2 cm, and so forth. In some embodiments, the distance L can be set based on the type of tissue 130, the size of the tumor and/or desired ablation zone, and so forth. The probe 110 can include a metal shaft, which is insulated except for an exposed conductive tip that is in direct electrical contact with the targeted tissue. An RF generator (not shown) can supply RF energy to the tissue 130 through the electrode 110. The setup 100 can include a reference electrode (not shown), which can be positioned at a conductive pad contacting the patient's skin in an area of relatively good electrical and thermal conductivity. The RF generator produces a RF voltage between the active RF electrode and the reference electrode, thereby establishing lines of electric field within the patient's body between the two electrodes. The electric field oscillates with the RF frequency (<1 MHz).

The TA 140 can be positioned in the organ 130 before ablation begins. The TA 140 can be dispensed and/or delivered from the electrode 110, as shown, though, in some embodiments, the TA 140 can be injected or otherwise delivered into the organ 130 via a syringe or a similar apparatus known to one skilled in the art. During ablation, the ions in the tissue move with the oscillating field and proportionately to the field intensity causing friction, which is converted into heat. That is, ions in the tissue can cause collision among surrounding molecules, such as neighboring sodium and chloride ions. The collisions of these molecules generate kinetic energy, which can turn into heat. The TA 140 can exhibit similar oscillating properties, but at two or more orders of magnitude higher than the ions, which can generate significantly more heat than the ions, resulting in the increased ablation observed when the TA 140 is used.

Successful RF ablation of an entire tumor typically occurs at temperatures of greater than about 60° C. throughout the target area. In some embodiments, however, poor tissue penetration by certain electrodes can result in an inability to ablate tumors larger than 1 cm in diameter. Illustrative embodiments overcome these inherent problems by ablating larger tumors (e.g., larger than 1 cm) with multiple electrodes, multiple-hook electrodes, bipolar arrays, cooled-tip electrodes, and/or pulsed RF probes. In some embodiments, poor energy penetrations also can be improved by altering tissue dielectric properties. For example, various concentrations in a contiguous injection of saline solutions have shown a marked improvement in the larger ablation volume. Saline volume and concentration influence coagulation diameter in a non-linear fashion as increased saline concentration can increase electrical conductivity (which is inversely proportional to the measured impedance) and enable greater energy deposition in tissues without inducing deleterious high temperatures at the electrode surface. This effect is non-linear with markedly increased tissue conductivity decreasing tissue heating. The increased conductivity can be beneficial for RF ablation in that it enables increased energy deposition which increases tissue heating. However, given less intrinsic electrical resistance, increased tissue conductivity also increases the energy required to heat a given volume of tissue. When this amount of energy cannot be delivered (e.g., it is beyond the maximum generator output), the slope is negative and less tissue heating (and coagulation) will result. Thus, to achieve clinical benefit (i.e., an increase in RF induced coagulation), optimal parameters for saline injection need to be determined for each type of RF apparatus used and for the different tumor types and tissues to be treated.

A drawback of saline solution to improve RF ablation involves its discrepancy of geometry of ablation. Specifically, the saline solution is drained to the directions with the least resistance, which results in an uncontrolled shape of ablation with increased risk of collateral injury to adjacent organs or tissue, e.g., bile duct, diaphragm, nerves. Use of TA during RF ablation can mitigate these effects and increase a volume of the ablation zone as desired.

The impact of TA on a change of temperature of an ablation zone during RF ablation can be seen in the following examples:

Example 6

Radiofrequency Ablation of an Ex Vivo Swine Liver.

A radiofrequency system (Viva combo RF Generator, STARmed, Goyang, S. Korea) was used for all ablation procedures at a power of 35 W with a continuous mode for 10 minutes (FIG. 2). The RF applicator (15G 2 cm ActiveTip) has perfusion ports at the tip through which 2 mL of TA were injected. The temperature change was measured 1.5 cm away in the transverse plane from the RF electrode. The thermocouple 120 was at the same depth as the RF electrode 110 tip as shown in FIG. 12. The experiments were repeated four times for control and TA, and the data were comparatively plotted and statistically analyzed (GraphPad PRISM® Version 6e).

Figure 13:
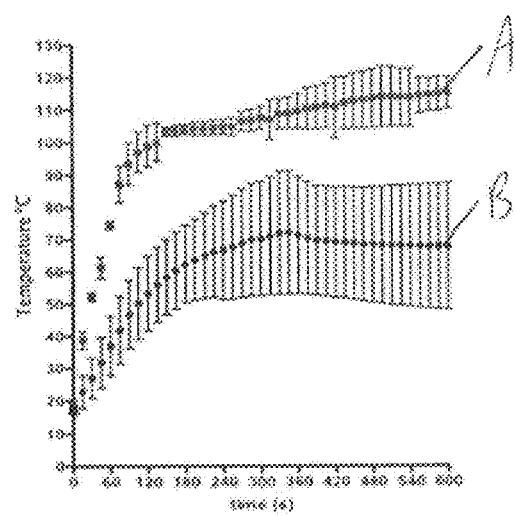
FIG. 13 illustrates temperature profiles of radiofrequency ablation using TA and control setups.

A total of 8 RF ablations were performed (four TA, four control). Overall, ablations performed using TA demonstrated a significantly higher rate of temperature increase than control, especially in the first 90 sec. During this period, the temperature increase was analyzed for linearity: control and TA (R square: 0.6695 and 0.9679, respectively). The slope of the rate was $0.3239 \pm 0.0446°$ C./s for control and $0.8178 \pm 0.0342°$ C./s for TA, respectively. Post-90 sec, temperature increase for both control and TA was slowed to ca. 70° C. and 110° C., respectively. Furthermore, the temperature variations for control appear to be significantly larger than TA throughout the measured period as shown in FIG. 13, which illustrates temperature profiles of radiofrequency ablation with the TA (A) and control (B). As shown, the temperature of the ablation with the TA (A) is higher than the control (B) throughout the duration of the ablation.

Example 7

Comparison of Ablation Zone Temperature Between TA and Various NaCl Solutions

Figure 14:
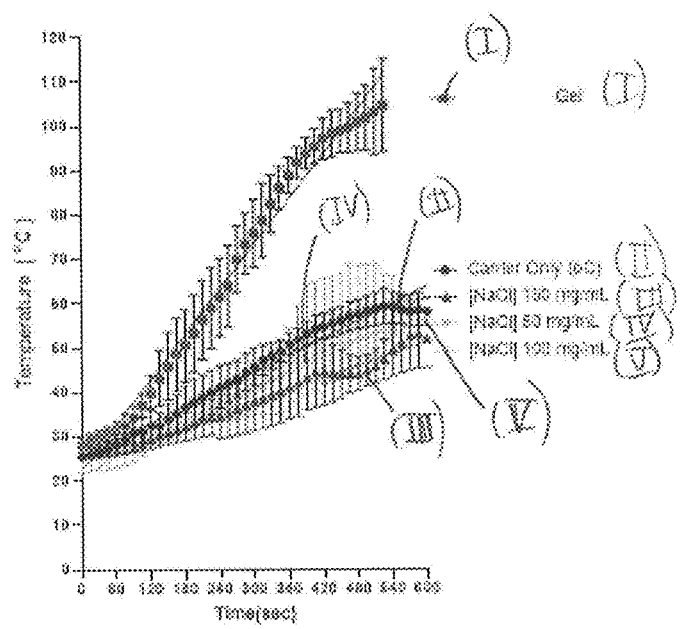
FIG. 14 illustrates temperature profiles of TA samples having varying concentrations over time.

Use of the TA can accelerate the ablation zone temperature change measured at a distance from the probe during RF ablation. For example, results of an RF ablation at a distance of 1 centimeter from the probe 110 in the bovine liver are shown in FIG. 14. The OsteoCool™ RF Ablation system (Medtronic Memphis Tenn.) was used for all ablation procedures with the following settings: ablation time 10 minutes; set temperature 95° C.; power limit 20 W; impedance cut off 50Ω. The RF applicator (18G, 2 cm ActiveTip) was placed to the same site where a TA sample (1 mL) was injected. The TA samples are, 1) HeatSYNC Gel, 2) carrier biopolymer, 3) aqueous NaCl solutions with 50, 100, 150 mg/mL. The temperature change was measured 1.0 cm away from the RF applicator at the same depth as the applicator's tip. The experiments were repeated four times for all samples and the obtained data were comparatively plotted and analyzed by using a biostatistics software (GraphPad PRISM® Version 8). As a result, a total of 20 RF ablations were performed: five samples (each n=4). Ablations with the TA (I) showed a significantly higher rate of temperature increase than all other samples (III, IV, V) including a biocarrier sample (II).

In some embodiments, the TA can be used as a cauterizing agent. Once the RF energy heats the TA to a specific temperature, e.g., >80° C., the TA can coagulate and become integral with the ablated tissue. For example, the TA can be applied to a tissue or organ to augment heating of said tissue or organ and/or to cauterize the site to prevent bleeding. The TA can be applied as a gel to one or more surfaces thereof such that heating the TA merges with the ablated tissue to seal up the site.

Figure 15:
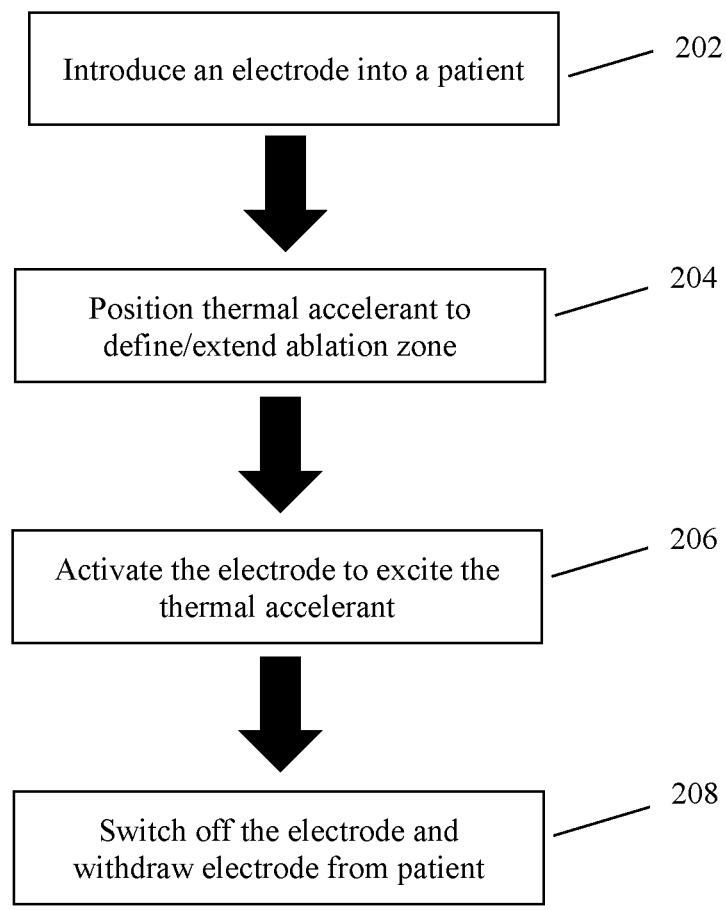
FIG. 15 illustrates a flowchart of an exemplary method using the compositions and systems disclosed herein.

FIG. 15 illustrates an exemplary method 200 of tissue ablation in accordance with the illustrative embodiments. It should be noted that, as described, this process is simplified from a longer process that normally would be used to perform an ablation. Accordingly, the process can have additional steps that those skilled in the art likely would use. In addition, some of the steps may be performed in a different order than that shown, or at the same time. Those skilled in the art therefore can modify the process as appropriate. Moreover, as noted above and below, materials and structures noted are but one of a wide variety of different materials and structures that may be used. Those skilled in the art can select the appropriate materials and structures depending upon the application and other constraints. Accordingly, discussion of specific materials and structures is not intended to limit all embodiments.

The process 200 can begin at step 202 by introducing one or more electrodes 110 into a body of a patient to reach a target site. The target site can include a tissue, organ, tumor, and so forth. After insertion, the electrode 110 can be disposed within the target site, proximate to the target site, and/or extending through the target site. Next, the thermal accelerant 140 can be positioned within the body of the patient at a distance from the electrode (step 204). The thermal accelerant 140 can be positioned so as to define and/or extend an ablation zone for the target site. The relative distances between the TA 140, the electrode 110, and the target site 130 can vary based on the desired ablation zone, patient anatomy, the size of the target site, and so forth, as discussed in detail above. In some embodiments, a second electrode or a second thermal accelerant can be added to the target site, as discussed above, to maximize the ablation zone.

After positioning the thermal accelerant 140, the electrode 110 can be activated to excite the TA (step 206). In some embodiments, the electrode 110 can include one or more energy emitting devices (not shown) thereon to excite particles of the TA to a specific temperature. A person skilled in the art will recognize that the energy emitting devices can utilize one or more of microwave, radiofrequency, and electroporation to perform the excitation. In some embodiments, heating the TA can cause the TA to cauterize to the target site by coagulating to become integral with the ablated tissue. Heating of the TA can continue until it the target site has become sufficiently ablated. After ablation is performed, the electrode can be switched off and withdrawn from the patient (step 208).

The invention being thus described, further variations, modifications and examples thereof will be understood by one of ordinary skill in the art and all such variations and modifications are deemed to be within the scope of the invention described and claimed herein.

The invention claimed is:

1. A composition for use in ablation, the composition comprising:
a thermal accelerant having:
   a polymer configured to become gelatinous or solidify at body temperature or above to become relatively immobilized after positioned within the target site;
   a chaotrope configured to adjust charge distribution within the polymer; and
   an imaging component configured to allow image-guided verification of the thermal accelerant within a body of a patient,
wherein the thermal accelerant, when exposed to an amount of ablative energy, has values of electrical conductivity and loss factor that are up to 5 times or greater than values of electrical conductivity and loss factor in living tissue when exposed to an equal amount of ablative energy without thermal accelerant.

2. The thermal accelerant of claim 1, wherein the viscosity of the thermal accelerant ranges from approximately 50 centiPoise to approximately 25,000 centiPoise.

3. The thermal accelerant of claim 1, wherein the chaotrope is selected from the group consisting of: calcium chloride, cesium chloride, lithium chloride, potassium chloride, rubidium chloride, sodium chloride, sodium citrate, and a combination thereof.

4. The thermal accelerant of claim 3, wherein the cesium chloride tumbles synchronously to the alternating electric field fueled by its intrinsic dipole moment to generate heat.

5. The thermal accelerant of claim 1, wherein the polymer comprises one or more of albumin, DNA, RNA, glycoproteins or glycopolymers such as IgA, IgG, or other immunoglobulins.

* * * * *